(12) United States Patent
Flynt et al.

(10) Patent No.: US 9,367,668 B2
(45) Date of Patent: Jun. 14, 2016

(54) DYNAMIC FITNESS EQUIPMENT USER INTERFACE ADJUSTMENT

(75) Inventors: David W. Flynt, Lake Forest Park, WA (US); Salman A. Khilji, Bellevue, WA (US); Piet H. Schouten, Redmond, WA (US); James S. Birrell, Seattle, WA (US)

(73) Assignee: Precor Incorporated, Woodinville, WA (US)

( * ) Notice: Subject to any disclaimer, the term of this patent is extended or adjusted under 35 U.S.C. 154(b) by 243 days.

(21) Appl. No.: 13/407,543

(22) Filed: Feb. 28, 2012

(65) Prior Publication Data
US 2013/0225370 A1    Aug. 29, 2013

(51) Int. Cl.
| | | |
|---|---|---|
| *A63B 24/00* | (2006.01) | |
| *A63B 71/00* | (2006.01) | |
| *A63B 15/02* | (2006.01) | |
| *G06F 19/00* | (2011.01) | |
| *A63B 71/06* | (2006.01) | |
| *A63B 22/00* | (2006.01) | |
| *A63B 22/02* | (2006.01) | |
| *A63B 22/06* | (2006.01) | |
| *A63B 23/02* | (2006.01) | |
| *A63B 23/04* | (2006.01) | |

(52) U.S. Cl.
CPC ........ *G06F 19/3481* (2013.01); *A63B 24/0087* (2013.01); *A63B 71/0622* (2013.01); *A63B 22/0056* (2013.01); *A63B 22/0076* (2013.01); *A63B 22/02* (2013.01); *A63B 22/0605* (2013.01); *A63B 23/0205* (2013.01); *A63B 23/0405* (2013.01); *A63B 2022/067* (2013.01); *A63B 2022/0682* (2013.01); *A63B 2023/0411* (2013.01); *A63B 2071/0644* (2013.01); *A63B 2071/0658* (2013.01); *A63B 2071/0675* (2013.01); *A63B 2220/13* (2013.01); *A63B 2220/18* (2013.01); *A63B 2220/30* (2013.01); *A63B 2220/62* (2013.01); *A63B 2225/20* (2013.01); *A63B 2225/50* (2013.01); *A63B 2230/062* (2013.01); *A63B 2230/755* (2013.01)

(58) Field of Classification Search
USPC ....................................................... 482/1, 4, 8
See application file for complete search history.

(56) References Cited

U.S. PATENT DOCUMENTS

| | | | |
|---|---|---|---|
| 4,512,567 A | 4/1985 | Phillips | 272/73 |
| 4,637,605 A | 1/1987 | Ritchie | 272/73 |
| 4,720,789 A | 1/1988 | Hector et al. | 463/33 |
| 4,828,257 A | 5/1989 | Dyer et al. | 482/5 |
| 4,840,372 A | 6/1989 | Oglesby et al. | 482/9 |
| 4,955,602 A | 9/1990 | Rastelli | 482/84 |
| 4,976,435 A | 12/1990 | Shatford et al. | 273/148 |
| 4,998,725 A | 3/1991 | Watterson et al. | 482/6 |
| 5,062,626 A | 11/1991 | Dalebout et al. | 482/1 |
| 5,062,632 A | 11/1991 | Dalebout et al. | 482/7 |
| 5,067,710 A | 11/1991 | Watterson et al. | 482/3 |
| 5,104,120 A | 4/1992 | Watterson et al. | 482/5 |

(Continued)

FOREIGN PATENT DOCUMENTS

| | | |
|---|---|---|
| EP | 1 252 915 | 4/2002 |
| GB | 2 279 577 | 1/1995 |
| WO | WO 2009/107904 | 9/2009 |
| WO | WO 2011/083434 | 7/2011 |

*Primary Examiner* — Stephen Crow
*Assistant Examiner* — Shila Jalalzadeh Abyane
(74) *Attorney, Agent, or Firm* — Terence P. O'Brien; Todd A. Rathe

(57) ABSTRACT

A method and exercise system obtain at least one parameter of ongoing exercise on a fitness equipment unit and adjust at least one operational characteristic of the user interface while a person is exercising and based upon the obtained at least one parameter of ongoing exercise.

18 Claims, 10 Drawing Sheets

(56) References Cited

U.S. PATENT DOCUMENTS

| | | | |
|---|---|---|---|
| 5,149,084 A | 9/1992 | Dalebout et al. | 482/3 |
| 5,213,555 A | 5/1993 | Hood et al. | 482/57 |
| 5,364,271 A | 11/1994 | Aknin et al. | 434/61 |
| 5,383,826 A | 1/1995 | Michael | 482/3 |
| 5,466,200 A | 11/1995 | Ulrich et al. | 482/4 |
| 5,484,355 A | 1/1996 | King, II et al. | 482/4 |
| 5,489,249 A | 2/1996 | Brewer et al. | 482/5 |
| 5,512,025 A | 4/1996 | Dalebout et al. | 482/6 |
| 5,554,033 A | 9/1996 | Bizzi et al. | 434/247 |
| 5,591,104 A | 1/1997 | Andrus et al. | 482/7 |
| 5,645,509 A | 7/1997 | Brewer et al. | 482/4 |
| 5,645,513 A | 7/1997 | Haydocy et al. | 482/57 |
| 5,655,997 A | 8/1997 | Greenberg et al. | 482/5 |
| 5,706,822 A | 1/1998 | Khavari | 600/483 |
| 5,777,895 A | 7/1998 | Kuroda et al. | 702/188 |
| 5,779,596 A | 7/1998 | Weber | 482/4 |
| 5,785,632 A | 7/1998 | Greenberg et al. | 482/5 |
| 5,888,172 A | 3/1999 | Andrus et al. | 482/7 |
| 5,890,995 A | 4/1999 | Bobick et al. | 482/4 |
| 5,916,063 A | 6/1999 | Alessandri | 482/4 |
| 5,931,763 A | 8/1999 | Alessandri | 482/4 |
| 6,042,519 A | 3/2000 | Shea | 482/57 |
| 6,053,844 A | 4/2000 | Clem | 482/8 |
| 6,059,692 A | 5/2000 | Hickman | 482/8 |
| 6,066,075 A | 5/2000 | Poulton | 482/8 |
| 6,152,856 A | 11/2000 | Studor et al. | 482/8 |
| 6,159,131 A | 12/2000 | Pfeffer | 482/8 |
| 6,171,218 B1 | 1/2001 | Shea | 482/57 |
| 6,193,631 B1 | 2/2001 | Hickman | 482/8 |
| 6,227,968 B1 | 5/2001 | Suzuki et al. | 463/7 |
| 6,244,988 B1* | 6/2001 | Delman | A63B 71/0622 482/8 |
| 6,312,363 B1 | 11/2001 | Watterson et al. | 482/54 |
| 6,330,499 B1 | 12/2001 | Chou et al. | 701/33 |
| 6,336,891 B1 | 1/2002 | Fedrigon et al. | 482/8 |
| 6,393,301 B1 | 5/2002 | Oda | 455/557 |
| 6,421,571 B1 | 7/2002 | Spriggs et al. | 700/17 |
| 6,447,424 B1 | 9/2002 | Ashby et al. | 482/8 |
| 6,458,060 B1 | 10/2002 | Watterson et al. | 482/54 |
| 6,464,618 B1 | 10/2002 | Shea | 482/8 |
| 6,475,115 B1 | 11/2002 | Candito et al. | 482/4 |
| 6,514,199 B1 | 2/2003 | Alessandri | 600/300 |
| 6,535,123 B2 | 3/2003 | Sandelman et al. | 340/506 |
| 6,554,706 B2 | 4/2003 | Kim et al. | 463/36 |
| 6,572,512 B2 | 6/2003 | Anderson et al. | 482/51 |
| 6,601,016 B1 | 7/2003 | Brown et al. | 702/182 |
| 6,616,578 B2 | 9/2003 | Alessandri | 482/8 |
| 6,626,799 B2 | 9/2003 | Watterson et al. | 482/4 |
| 6,626,800 B1 | 9/2003 | Casler | 482/8 |
| 6,634,992 B1 | 10/2003 | Ogawa | 482/8 |
| 6,638,198 B1 | 10/2003 | Shea | 482/8 |
| 6,659,916 B1 | 12/2003 | Shea | 482/57 |
| 6,690,940 B1 | 2/2004 | Brown et al. | 455/456.4 |
| 6,702,719 B1 | 3/2004 | Brown et al. | 482/8 |
| 6,746,371 B1 | 6/2004 | Brown et al. | 482/8 |
| 6,827,669 B2 | 12/2004 | Cohen et al. | 482/8 |
| 6,863,641 B1 | 3/2005 | Brown et al. | 482/8 |
| 6,866,613 B1 | 3/2005 | Brown et al. | 482/8 |
| 6,902,513 B1 | 6/2005 | McClure | 482/8 |
| 6,918,858 B2 | 7/2005 | Watterson et al. | 482/54 |
| 6,921,351 B1 | 7/2005 | Hickman et al. | 482/8 |
| 6,926,646 B1 | 8/2005 | Nguyen | 482/71 |
| 6,971,973 B2 | 12/2005 | Cohen et al. | 482/8 |
| 6,991,586 B2 | 1/2006 | Lapcevic | 482/8 |
| 6,997,852 B2 | 2/2006 | Watterson et al. | 482/1 |
| 7,022,047 B2 | 4/2006 | Cohen et al. | 482/8 |
| 7,056,265 B1 | 6/2006 | Shea | 482/8 |
| 7,060,006 B1 | 6/2006 | Watterson et al. | 482/54 |
| 7,060,008 B2 | 6/2006 | Watterson et al. | 482/54 |
| 7,070,539 B2 | 7/2006 | Brown et al. | 482/8 |
| 7,121,982 B2 | 10/2006 | Feldman | 482/8 |
| 7,128,693 B2 | 10/2006 | Brown et al. | 482/8 |
| 7,166,062 B1 | 1/2007 | Watterson et al. | 482/8 |
| 7,166,064 B2 | 1/2007 | Watterson et al. | 482/54 |
| 7,217,224 B2 | 5/2007 | Thomas | 482/8 |
| 7,331,226 B2 | 2/2008 | Feldman et al. | 73/379.01 |
| 7,455,622 B2 | 11/2008 | Watterson et al. | 482/8 |
| 7,491,153 B2 | 2/2009 | Li et al. | 482/8 |
| 7,507,183 B2 | 3/2009 | Anderson et al. | 482/1 |
| 7,521,623 B2 | 4/2009 | Bowen | 84/612 |
| 7,537,546 B2 | 5/2009 | Watterson et al. | 482/8 |
| 7,549,947 B2 | 6/2009 | Hickman et al. | 482/8 |
| 7,556,590 B2 | 7/2009 | Watterson et al. | 482/8 |
| 7,575,536 B1 | 8/2009 | Hickman et al. | 482/8 |
| 7,594,873 B2 | 9/2009 | Terao et al. | 482/1 |
| 7,618,346 B2 | 11/2009 | Crawford et al. | 482/8 |
| 7,645,213 B2 | 1/2010 | Watterson et al. | 482/4 |
| 7,705,230 B2 | 4/2010 | Bowen | 84/636 |
| 7,711,355 B1 | 5/2010 | Kruger et al. | 455/471 |
| 7,758,469 B2 | 7/2010 | Dyer et al. | 482/4 |
| 7,766,794 B2 | 8/2010 | Oliver et al. | 482/8 |
| 7,841,966 B2 | 11/2010 | Aaron et al. | 482/8 |
| 7,857,731 B2 | 12/2010 | Hickman et al. | 482/8 |
| 7,927,253 B2 | 4/2011 | Vincent et al. | 482/8 |
| 7,931,563 B2 | 4/2011 | Shaw et al. | 482/9 |
| 7,967,730 B2 | 6/2011 | Crawford et al. | 482/8 |
| 7,985,164 B2 | 7/2011 | Ashby | 482/8 |
| 8,029,415 B2 | 10/2011 | Ashby et al. | 482/8 |
| 8,038,577 B2 | 10/2011 | McIntosh | 482/4 |
| 8,047,966 B2 | 11/2011 | Dorogusker et al. | 482/8 |
| 8,103,517 B2 | 1/2012 | Hinnebusch | 482/8 |
| 8,118,709 B2 | 2/2012 | McKirdy et al. | 482/1 |
| 8,152,693 B2 | 4/2012 | Nurmela et al. | 705/2 |
| 8,162,804 B2 | 4/2012 | Tagliabue | 482/9 |
| 2001/0001303 A1 | 5/2001 | Ohsuga et al. | 482/5 |
| 2002/0019258 A1 | 2/2002 | Kim et al. | 463/36 |
| 2002/0055383 A1 | 5/2002 | Onda et al. | 463/36 |
| 2004/0005924 A1 | 1/2004 | Watabe et al. | 463/36 |
| 2004/0043367 A1 | 3/2004 | Chou | 434/250 |
| 2006/0229162 A1 | 10/2006 | Choy | 482/4 |
| 2007/0219059 A1 | 9/2007 | Schwartz et al. | 482/8 |
| 2007/0225118 A1 | 9/2007 | Giorno et al. | 482/1 |
| 2007/0254778 A1 | 11/2007 | Ashby | 482/5 |
| 2007/0265139 A1 | 11/2007 | Glick | 482/8 |
| 2008/0051256 A1 | 2/2008 | Ashby et al. | 482/5 |
| 2008/0119332 A1* | 5/2008 | Roman | A63B 71/0622 482/54 |
| 2008/0161161 A1 | 7/2008 | Pipinich et al. | 482/8 |
| 2008/0161654 A1 | 7/2008 | Teller et al. | 600/300 |
| 2008/0171636 A1* | 7/2008 | Usui | A63B 24/0062 482/8 |
| 2008/0207401 A1 | 8/2008 | Harding et al. | 482/4 |
| 2008/0214357 A1 | 9/2008 | Farinelli et al. | 482/8 |
| 2008/0314851 A1 | 12/2008 | Jacoby | 211/149 |
| 2009/0023553 A1 | 1/2009 | Shim | 482/4 |
| 2009/0075781 A1 | 3/2009 | Schwarzberg et al. | 482/8 |
| 2009/0098980 A1 | 4/2009 | Waters | 482/8 |
| 2009/0098981 A1 | 4/2009 | Del Giorno | 482/9 |
| 2009/0111656 A1 | 4/2009 | Sullivan et al. | 482/4 |
| 2009/0144080 A1 | 6/2009 | Gray et al. | 705/2 |
| 2009/0156363 A1* | 6/2009 | Guidi | A63B 71/0619 482/4 |
| 2009/0156364 A1 | 6/2009 | Simeoni | 482/9 |
| 2009/0219159 A1 | 9/2009 | Morgenstern | 340/573.1 |
| 2009/0233771 A1 | 9/2009 | Quatrochi et al. | 482/9 |
| 2009/0239709 A1 | 9/2009 | Wu | 482/8 |
| 2009/0240113 A1 | 9/2009 | Heckerman | 600/300 |
| 2009/0262088 A1 | 10/2009 | Moll-Carrillo et al. | 345/173 |
| 2009/0269728 A1 | 10/2009 | Verstegen et al. | 434/247 |
| 2010/0137104 A1* | 6/2010 | Speronati Laghi | A63B 22/0235 482/4 |
| 2010/0179028 A1* | 7/2010 | Watterson | A63B 22/00 482/9 |
| 2012/0041767 A1* | 2/2012 | Hoffman | A63B 24/0059 705/1.1 |
| 2012/0046144 A1* | 2/2012 | Lin | A63B 71/0622 482/8 |

\* cited by examiner

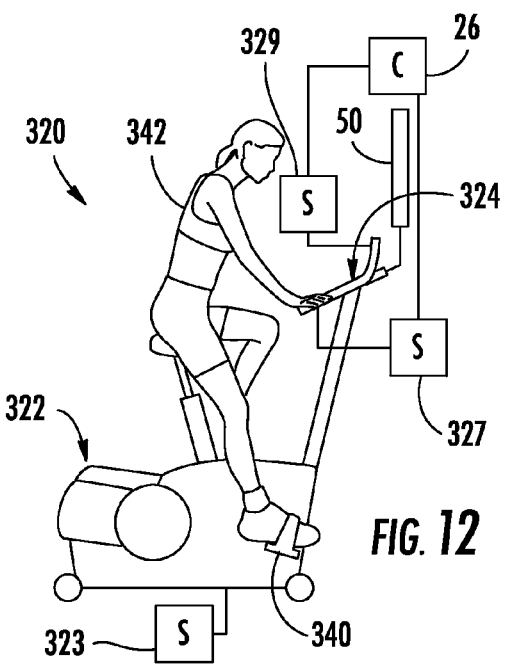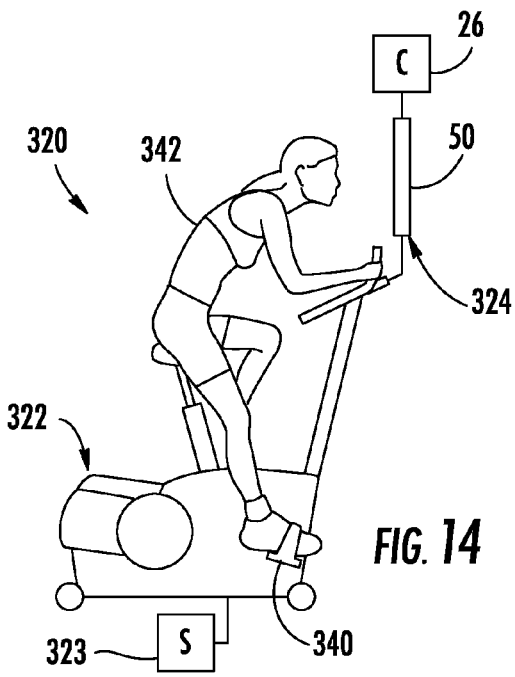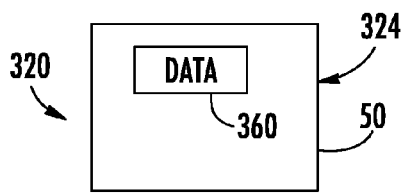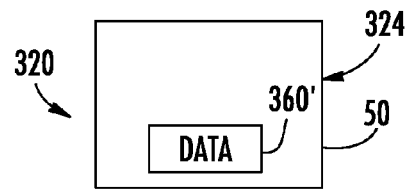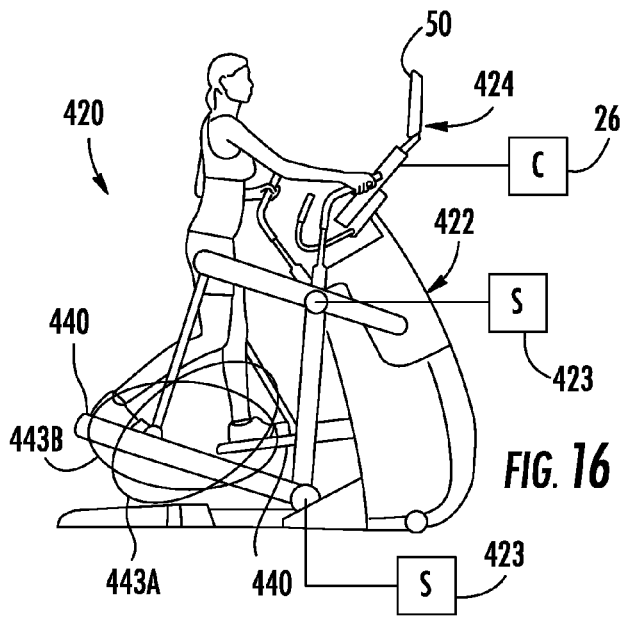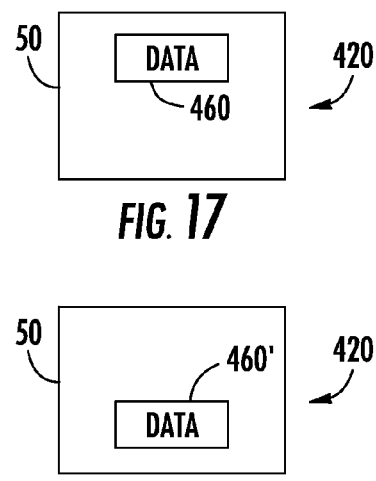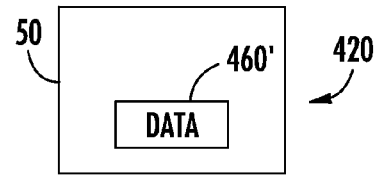

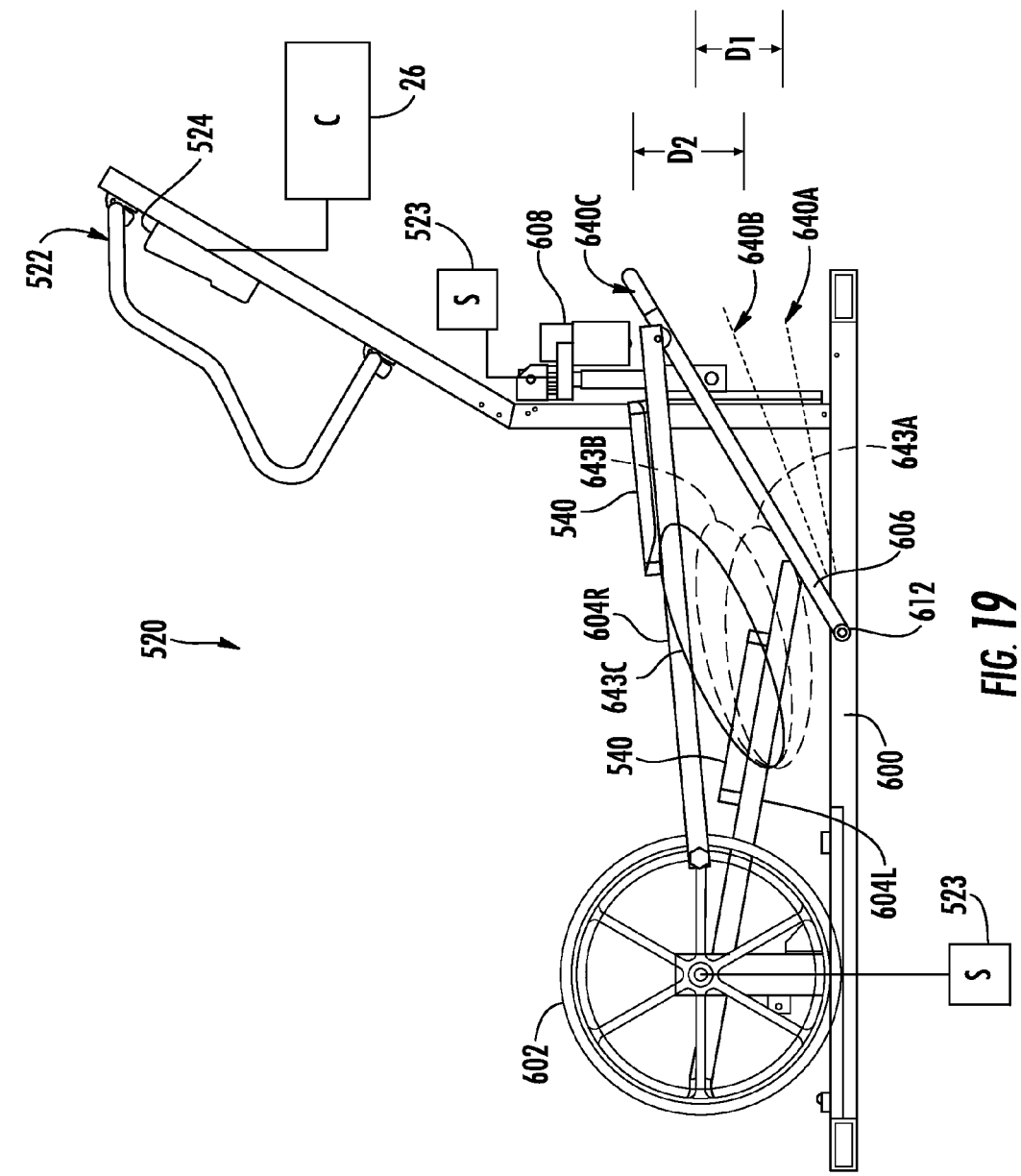
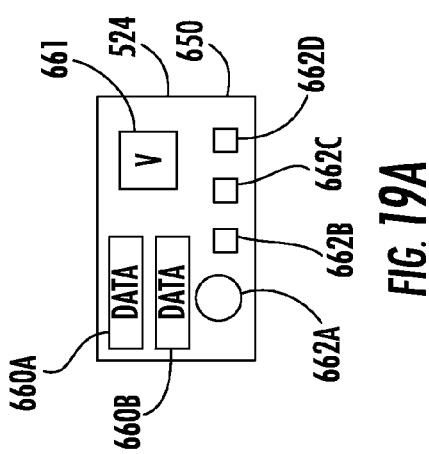
FIG. 19A
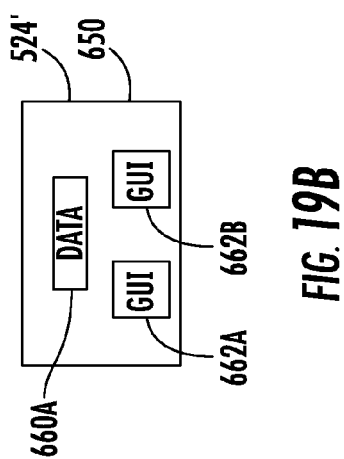
FIG. 19B
FIG. 19

DYNAMIC FITNESS EQUIPMENT USER INTERFACE ADJUSTMENT

BACKGROUND

During exercise on a fitness equipment unit, a person's ability to engage and interact with various user interface elements may change. As a result, during ongoing exercise, a person may find himself or herself no longer being able to optimally interact with the fitness equipment unit or various user interfaces.

BRIEF DESCRIPTION OF THE DRAWINGS

FIG. 12 is a side elevation view of another example implementation of the exercise system of FIG. 1, illustrating a person in an upright posture during exercise.

FIG. 13 is a schematic illustration of a user interface being presented while the person is in the upright posture in FIG. 12.

FIG. 14 is a side elevation view of the exercise system of FIG. 12, illustrating a person in an angled, leaning posture during exercise.

FIG. 15 is a schematic illustration of the user-interface being presented while the person is in the leaning posture in FIG. 14.

FIG. 16 is a side elevation view of another example implementation of the exercise system of FIG. 1, illustrating two example selectable paths for movable members.

FIG. 17 is a schematic illustration of a user interface being presented while a first one of the paths is being taken by the movable members.

FIG. 18 is a schematic illustration of the user-interface being presented while a second one of the paths is being taken by the movable members.

FIG. 19 is a side elevation view of another example implementation of the exercise system of FIG. 1.

FIG. 19A is a schematic illustration of a first user interface is presented by the exercise system of FIG. 19.

FIG. 19B is a schematic illustration of a second user interface is presented by the exercise system of FIG. 19.

DETAILED DESCRIPTION OF THE EXAMPLE EMBODIMENTS

Figure 1:
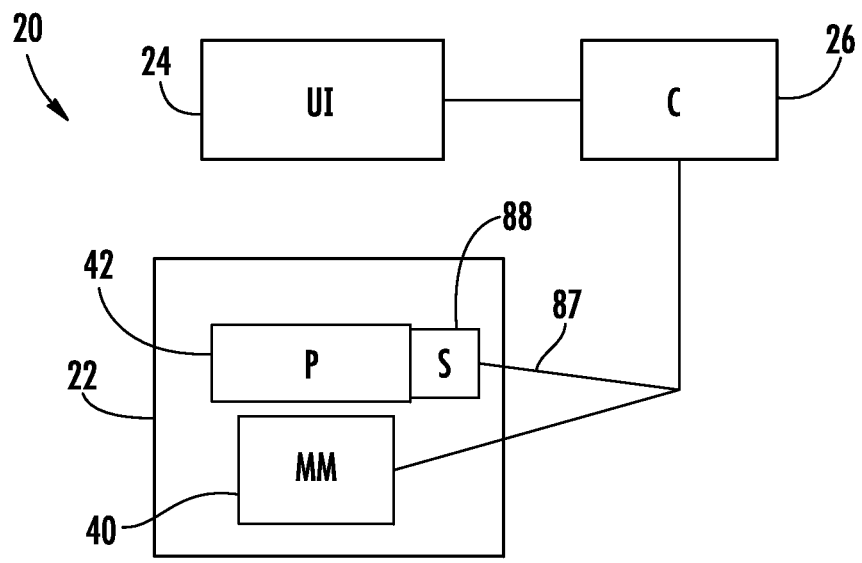
FIG. 1 is a schematic illustration of an example exercise system which automatically or dynamically adjusts user interface operational characteristics based upon ongoing exercise parameters.

FIG. 1 schematically illustrates an example exercise system 20 which comprises a fitness equipment unit 22, a user interface 24 and a controller 26. As will be described hereafter, controller 26 dynamically adjusts one or more operational characteristics of user interface 24 based upon characteristics or parameters of ongoing exercise. Such dynamic adjustment enables a person to better interact with fitness equipment unit 22 to provide a safer and more productive exercise session.

Fitness equipment unit 22 comprises a machine or device with which a person interacts to carry out cardiovascular exercise, anaerobic exercise or combinations thereof. As schematically shown by FIG. 1, fitness equipment unit 22 comprises one or more movable members 40 which is adapted or configured to be contacted by an anatomy of a person 42 to facilitate exercise by the person 42. In some implementations, an adjustable or controlled resistance may be applied against movement of movable member 40. In some implementations, the size, shape or inclination of a path through which the movable member 40 moves may be controlled or adjusted.

In one implementation, movable member 40 may comprise a footpad against which a person's foot or feet press against during exercise. Examples of exercise devices that include such a footpad include, but are not limited to, elliptical machines, stepper machines, rowing machines, stationary bicycles, adaptive motion machines, ski simulation machines, and leg press machines. In one implementation, movable member 40 may comprise a belt against which the user contacts, such as those used in treadmills. In one implementation, movable member 40 may comprise a handgrip about which a person grasps to apply force during exercise. Examples of exercise devices that include such handgrips include, but are not limited to, elliptical machines (swing arms), stepper machines (swing aims), adaptive motion machines (swing arms), climbing machines, pendulum motion machines, ski simulation machines, rowing machines, weight pull down machines, bench press machines and the like. In one implementation, movable member 40 may comprise a member configured to contact other portions of an anatomy such as members that contact a person's shins (leg press), a person's shoulders (squat machine), or a person thighs (abdominal exercise machine).

Figure 2:
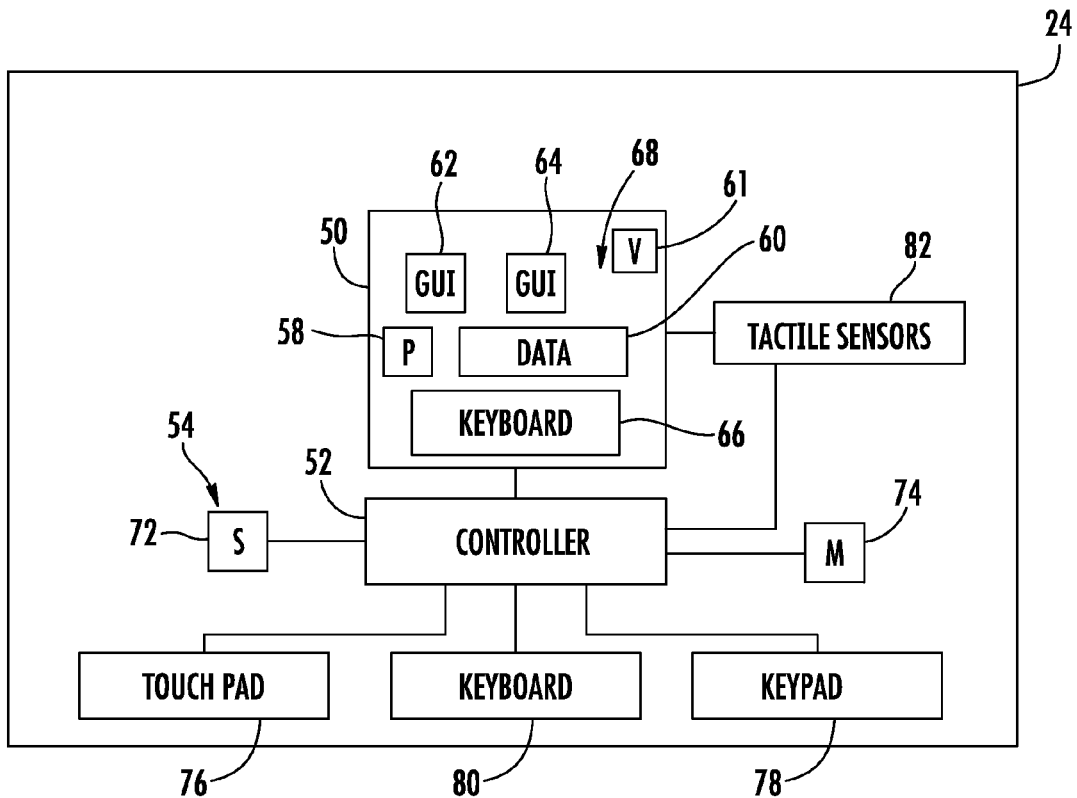
FIG. 2 is a schematic illustration of an example user interface of the system of FIG. 1.

User interface 24 comprises one or more devices with which a person interacts during exercise to receive information, content and/or input choices or selections. FIG. 2 schematically illustrates one example of user interface 24. In the example illustrated, user-interface 24 comprises display screen 50, controller 52 and manual interaction or input devices 54. Display screen 50 comprise a monitor, panel or other form of a screen either directly mounted to or formed as part of fitness equipment unit 22, supported independent of fitness equipment unit 22 at a position and location facilitating viewing by a person during exercise on fitness equipment unit 22 or held/portably supported for viewing during exercise (such as a portable hand held or electronic device (a personal data assistant, tablet, notebook, e-reader and the like)). As further schematically shown by FIG. 2, display screen 50 comprises a prompt area 58, one or more data areas 60, video areas or region 61, graphical user interfaces 62, 64 and 66, and pointer or cursor 68.

Prompt area 58 comprises that portion of display screen 50 by which alphanumeric symbols may be entered using one or more of manual input devices 54. Data areas 60 comprise areas or regions at which alphanumeric and/or graphical (e.g. stride dial) data is presented. Such data may comprise instructions for the use of fitness equipment unit 22, exercise results for fitness equipment unit 22 or information or news not pertaining to fitness equipment unit 22, such as news or information regarding business, sports and the like such as information supplied by a webpage. Video area 61 comprises a region or area of display screen 50 at which videos are presented. Such videos may present video information pertaining to fitness equipment unit 22, information pertaining to a health club or fitness facility at which fitness equipment unit 22 is located or information unrelated to fitness community 22 or a fitness facility, such as news, sports, entertainment, movies and the like.

Graphical user interfaces 62, 64 and 66 comprise graphical icons or graphical depictions presented on display screen 50 which may be selected by a user to input a choice or selection to fitness equipment unit 22 and/or controller 26 (shown in FIG. 1). In the example illustrated, graphical user interfaces 62, 64 and 66 (or portions thereof) may be selected in one of two fashions: (A) by moving the pointer cursor 68 using a tool or device external to display screen 50 such as by using a stylus 72, a mouse 74, a touchpad 76, a keypad 78 or an external physical keyboard 80 or (B) by manually contacting (touching or sliding against) the graphical user interface 62, 64, 66 on display screen 50, whereby such manual physical contact with the surface of display screen 50 is sensed by tactile sensors 82 incorporated into display screen 50 (display screen 50 comprising a touch screen with a tactile sensors 82 comprising manual input devices). In the example illustrated, graphical user interface 66 is specifically configured as a keyboard, wherein alphanumeric inputs may be made by a person either manipulating and locating cursor 68 over individual keys of keyboard 66 using external manual inputs or by manually touching or contacting individual keys of keyboard 66 on display screen 50, such contact being sensed by tactile sensors 82.

In the example illustrated, each of the manual input devices 72, 74, 76, 78, 80 and 82 transmits signals to controller 52 which generates control signals to indicate such input and values are selections on display screen 50. In other implementations, each of such manual input devices may have a dedicated controller. In some implementations, controller 52 is the same as or part of controller 26 shown in FIG. 1. In the example illustrated, user interface 24 is illustrated as including multiple distinct manual interaction devices. In other implementations, user-interface 24 may include a greater or fewer of such manual interaction devices. For example, in some implementations, user interface 24 may alternatively comprise just display screen 50 and tactile sensors 82 providing all input or selections. In other implementations, user-interface 24 may alternatively comprise display screen 50 in one or more of the external manual inputs commenting tactile sensors 82, where display screen 50 is configured as a touch screen.

Figure 3:
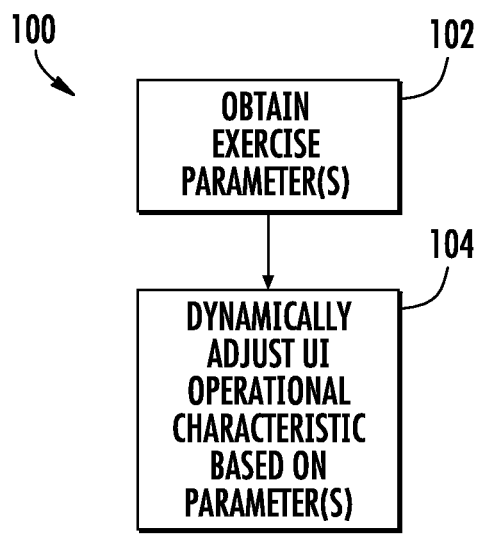
FIG. 3 is a flow diagram of a method for being carried out by the exercise system of FIG. 1.

As schematically shown in FIG. 1, controller 26 comprises one or more processing units programmed or configured to carry out the example method 100 shown in FIG. 3. For purposes of this application, the term "processing unit" shall mean a presently developed or future developed processing unit that executes sequences of instructions contained in a memory. Execution of the sequences of instructions causes the processing unit to perform steps such as generating control signals. The instructions or code may be loaded in or stored upon a non-transient computer-readable medium, such as a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 26 may be embodied as part of one or more application-specific integrated circuits (ASICs). Unless otherwise specifically noted, the controller is not limited to any specific combination of hardware circuitry and software, nor to any particular source for the instructions executed by the processing unit.

In one implementation, controller 26 and user-interface 24 are embodied as a single unit, wherein controller 26 controls user-interface 24 as well as one or more functions of fitness equipment unit 22. In another implementation, controller 26 may be provided remotely from user-interface 24 and fitness equipment unit 22, wherein controller 26 communicates with user-interface 24 and fitness equipment unit 22 across a wired or wireless connection. In one implementation, controller 26 may be provided at the fitness equipment facility housing fitness community 22. In another implementation, controller 26 may be located in what is known as the "cloud".

As indicated by step 102 in FIG. 3, controller 26 obtains at least one exercise parameter during ongoing exercise (while the person is exercising). As indicated by step 104 in FIG. 3, controller 26 uses the one or more obtained exercise parameters to dynamically adjust user-interface 24. The phrase "dynamic" refers to the ability of controller 26 to adjusts operational characteristics of user-interface 24 on-the-fly while the person is exercising. As a result, controller 26 may dynamically change operational characteristics of user-interface 24 to enhance safety and/or interaction with user-interface 24 based upon the obtained exercise parameters.

In one implementation, controller 26 automatically adjusts or changes operational characteristics of user-interface 24 based upon one or more obtained exercise parameters. In such an implementation, after such changes are made, controller 26 may present a prompt or other means by which the person exercising may override the adjustments made to the user interface 24. In one implementation, all of the adjustments may be overridden, wherein user-interface 24 returns to the default state or returns to the state immediately preceding such adjustments. In another implementation, the user may be offered with prompts or other input opportunities to selectively choose which of the implemented changes to user-interface 24 may be maintained at which of the implemented changes to user-interface 24 are to be overridden.

In another implementation, controller 26 may provide the person exercising with the opportunity to override recommended changes to user-interface 24 prior to the implementation of such changes to user-interface 24. For example, controller 26 may visibly present a recommended change to user-interface 24, wherein implementation of the recommended change requires an input acceptance of the recommended change by the person exercising. In another example, controller 26 may visibly present a recommended change to the operational characteristics of user-interface 24, wherein implementation of the recommended change will automatically take place within a predefined time unless the person exercising inputs an objection or in override command. In one implementation, the visible presentation of the recommended change may simply be an identification of the suggested change. In another implementation, visible presentation of the recommended change may comprise a temporary preview of the actual changes such as by presenting a window depicting the new suggested format or appearance for user-interface 24.

In one implementation, the adjustment of user-interface 24 by controller 26 is bidirectional. In other words, changes to the operational characteristics of user-interface 24 may, in response to a first exercise parameter, result in the operational characteristics of user-interface 24 being changed or altered such be less complex and more easily interacted with by reducing data, reducing graphical user interfaces, and reducing or eliminating use of manual inputs of user-interface 24. In response to another exercise parameter, the operational characteristics of user-interface 24 may be changed or altered so as to be more complex, offering more data, more graphical user interfaces or allowing use of more manual inputs. For example, a person may be working out at a high intensity level, wherein certain data is no longer presented or wherein certain manual inputs or manual user interfaces (such as a physical or virtual keyboard for Internet or web surfing) are no longer provided. In response to the person reducing his or her exertion level, controller 26 may present or enable the previously on presented data or may present or enable one or more manual inputs or manual user interfaces to allow the person exercising to engage in more involved or more demanding interactions ever previously allowed when the person exercising was working out at a high-level. In such an implementation, controller 26 provides the person exercising with the ability to voluntarily and temporarily reduce his or her exertion level to temporarily enable or obtain the presentation of additional entertainment or data as well as the enablement of more involved manual inputs, such as the enablement of a virtual or physical keyboard to better allow the person to engage in activities such as Internet searches and the like.

In some implementations, controller 26 may be configured to invoke such changes to operational characteristics of user-interface 24 only after existing operational characteristics for user-interface 24 have been in place for predefined minimum period of time. For example, after the operational characteristics for user-interface 24 have been changed, a timer or clock may be triggered, inhibiting or preventing further changes to operational characteristic of user-interface 24 until the timer clock has expired or until a predefined period of time has elapsed. This built-in adjustment delay or adjustment override may reduce the potentially annoying continuous changing of the operational characteristics for user-interface 24 in those circumstances where the person is exercising at a level near a trigger point or threshold level.

Figure 4:
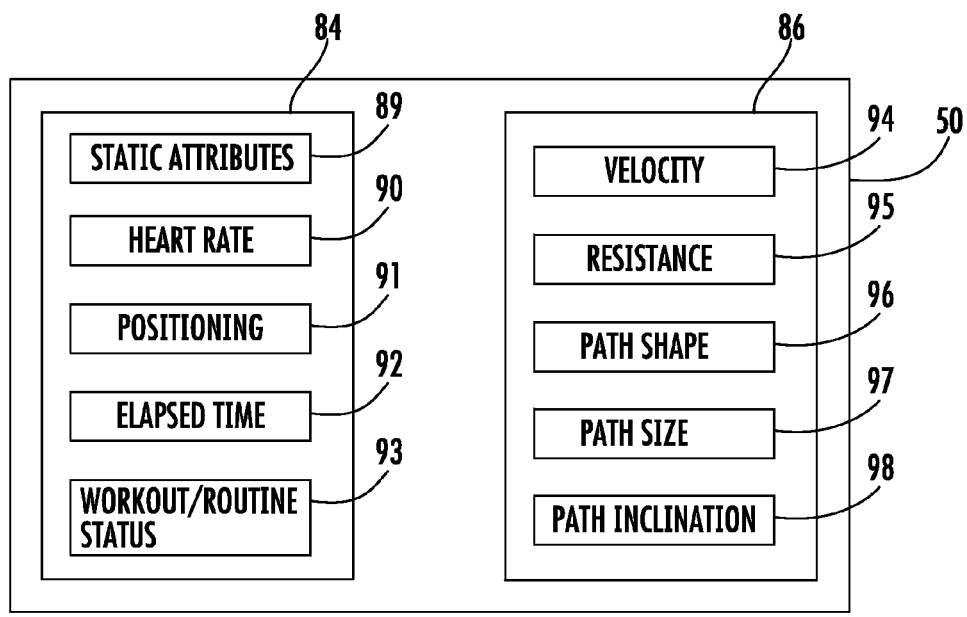
FIG. 4 is a schematic illustration of a display screen presenting exercise parameters for selection and use in the automatic adjustment of user interface operational characteristics.

In the example illustrated, exercise system 20 is operable in one of multiple user selectable modes, wherein the user may select or choose one or more exercise parameters upon which the adjustment of user-interface 24 is based. FIG. 4 illustrates one example of selections or settings that may be chosen by a person using exercise system 20. In particular, FIG. 4 illustrates an example display of exercise parameter options that are presented on display screen 50 (shown in FIG. 2) for selection by a person using one or more manual inputs 54. As shown by FIG. 4, such optional settings for exercise parameters are grouped into (A) personal exercise parameters 84 and (B) movable member exercise parameters 86.

Personal exercise parameters 84 comprise sensed values or characteristics pertaining to the person who is exercising. As indicated by communication branch 87 in FIG. 1, controller 26 is in communication with one or more sensors 88 that sense such personal exercise parameters 84 for the person 42 who is exercising on fitness equipment unit 22. In the example illustrated, controller 26 has sensors or is otherwise configured to provide a person with the option of selecting one or more of the following personal parameters for adjusting operational characteristics of user-interface 24: static attributes 89, heart rate 90, personal positioning 91, elapsed fitness equipment unit session time 92 and workout status 93.

Static attributes 89 comprise characteristics or attributes of the person which do not substantially change (weight loss or fitness level changes during an individual workout session may merely change to an insubstantial extent) and cannot be substantially changed during an individual exercise session on fitness equipment unit 22. Such attributes may be sensed by one or more sensors 88 or may be obtained by controller 26 by prompting the person exercising to enter such static attributes 89 or by retrieving such information from a stored personal profile or database of information for the particular person. Examples of static attributes 89 include, but are not limited to a person's characteristics such as age, eyesight, fitness level, health, pregnancy condition, glasses or contacts, right-handed or left-handed, prosthetic use, height, weight and body shape. Such static attributes 89 may be utilized by controller 26 alone or in combination with other parameters (examples of which are described hereafter) in turning whether to change operational characteristics of user-interface 24 and what changes or adjustments should be made to the operational characteristics of user-interface 24. For example, controller 26 may or adjust the location of a graphical user interface based at least in part upon whether the person exercising is right-handed or left-handed. Controller 26 may control or adjust the arrangement and size of data or graphic user interfaces depending upon whether the person exercising is relatively good or poor eyesight, is nearsighted, is farsighted or whether the person employees glasses or contacts. Controller 26 may control the arrangement of data or graphical user interfaces based at least in part upon the person's height. Controller 26 may take into account the person's age, health or fitness level and body shape when adjusting operational characteristics of user-interface 24 as a result of changes in the person's exertion level during an exercise session on fitness community 22.

Heart rate 90 comprises the heart rate of the person while the person is exercising upon fitness equipment unit 22. Heart rate 90 may be continuously monitored while the person is exercising using fitness community 22 using sensors built into handgrips of fitness equipment unit 22 or using heart rate sensing accessories position on the person exercising and connected to controller 26. In one implementation, in response to a sensed person's heart rate exceeding a predetermined threshold during exercise, controller 26 may generate control signals simplifying interaction with user-interface 24 is one of various manners (described hereafter).

Personal positioning 91 comprises a person's sensed orientation or determined ergonomic values based on sensing of a person's anatomy. For example, a person sensed orientation may be determined by sensors located in each of multiple handgrips or hand rests, wherein those sensors contacted by the person indicate or correspond to the person orientation on fitness community 22. For example, the person may have the option assuming an upright orientation or in leaning orientation. In such an implementation, controller 26 may utilize the sensed personal positioning 91 to adjust user-interface 24 to enhance viewing or to facilitate easier interaction with user-interface 24. As another example, different sensors 88 provided as part of fitness equipment unit 22 may indicate ergonomic values or metrics of the person exercising, such as his or her height, arm reach and the like. Controller 26 may utilize such determined ergonomic values to adjust operational characteristics of user-interface 24 to best fit the determined ergonomic characteristics of the person exercising. For example, controller 26 may differently adjust the positioning of graphical user interfaces 62, 64 depending upon whether the person is determined to be tall or short, using one or more predefined ergonomic thresholds or ranges.

Elapsed time 92 and workout status 93 comprise personal parameters that are not generally sensed, but which are obtained by controller 26 using the person's profile (retrieved from a memory or database) and the current status of the person on fitness equipment unit 22 (as calculated or determined by controller 26). For example, as a person approaches different stages during an exercise session on fitness community 22, he or she may become fatigued. Controller 26 may, at different stages during a session on fitness equipment unit 22, automatically adjust operational characteristics of user-interface 24. For example, user-interface 24 may include a fewer number of graphical user interfaces 62, 64, larger graphical user interfaces 62, 64 or alternative layout as compared to when the person begins the exercise session on fitness equipment unit 22. As a result, interaction with user-interface 24 is maintained despite possible lower levels of focus by the person exercising at the end of his or her session on fitness equipment unit 22.

Workout status comprises a personal parameter obtained by controller 26 based at least partially based upon how fitness equipment unit 22 fits into an overall exercise routine or workout on a particular day. In particular, upon retrieving a personal record for the person exercising identifying the person's exercise routine for the day and performance results on other fitness equipment units 22 (different types of exercise machines), controller 26 may adjust operational characteristics of user-interface 24. For example, controller 26 may differently adjust operational characteristics of user-interface 24 depending upon whether the use of fitness equipment unit 22 is determined to fall at the beginning of an overall workout routine or towards the end of an overall workout routine.

Movable member exercise parameters 86 comprise metrics or values pertaining to the one or more movable members 40 of fitness equipment unit 22 during exercise. In the example illustrated, exercise system 20 and controller 26 offer the following movable member exercise parameters 86 for adjusting operational characteristics of user-interface 24: velocity 94, resistance 95, path shape 96, path size 97 and path inclination 98.

Velocity 94 comprises the velocity at which movable member 40 is driven, by fitness equipment unit 22 such as the loss of the belt being driven by a treadmill or by the person exercising applying force to the movable member, such as the footpads or pedals of an elliptical machine, an adaptive motion machine, a stationary bicycle and the like. This velocity may be the actual velocity of the move member (1:1 proportion) or the velocity of a component of fitness equipment unit 22 that corresponds to or for proportional to the velocity of movable member 40 (a 1:1 proportion or other proportions less than or greater than 1:1). For example, instead of adjusting operational characteristics of user-interface 24 based upon the velocity of movable member 40, the operational characteristics of user-interface 24 may be adjusted based upon the velocity of other linkages, gears, belts or the like which are operably connected to move member 40 and which move in response to and in some proportion to the movable member 40. In one implementation, controller 26 may adjust the operational characteristics of user-interface 24 to simplify the complexity of user-interface 24 or to disable or otherwise discourage use of particular manual inputs 54 in response to the velocity of movable member 40 surpassing predefined and stored thresholds.

Resistance 95 comprises a varying or adjustable resistance applied against movement of movable member 40. In one implementation, controller 26 may adjust the operational characteristics of user-interface 24 to simplify the complexity of user-interface 24 or to disable or otherwise discourage use of particular manual inputs 54 in response to the resistance level surpassing predefined and stored thresholds.

Path shape 96 comprises the shape of the reciprocating or circuitous path chosen for and being taken by the least one movable member 40. For example, in some fitness equipment units, such as adaptive motion machines, permit a person to control and vary the shape of the path through which move members 40 move by the user simply adjusting the force that the user applies against the foot members 40. In other fitness equipment units, a person may adjust settings of the fitness equipment unit 22 such that the one or more move members 40 move through a selected one of a plurality of available path shapes. In response to the selection of the path shape parameter 96, controller 26 may adjust the operational characteristics of user interface 24 based upon the ongoing or current path shape being taken by the one or more movable members 40. For example, user-interface 24 may be provided with a first operational characteristic when movable members 40 are moving through a first elliptical path and may be provided with a second different operational characteristic when movable members are moving through a second elliptical path having a shape different than the shape of the first elliptical path.

Path size 97 refers to or comprises an amplitude of the path being taken by the one or more movable members 40. For example, one or more movable members 40 may move through identical paths at different times, but the paths may have different amplitudes or different sizes. In response to the selection of the path size parameter 97, controller 26 may adjust the operational characteristics of user interface 24 based upon the ongoing or current path size being taken by the one or more movable members 40. For example, user-interface 24 may be provided with a first operational characteristic when movable members 40 are moving through a first elliptical path having a first size and may be provided with a second different operational characteristic when movable members are moving through a second elliptical path having a second size different than the first size.

Path inclination 98 refers to or comprises the angle of the path (with respect to a horizontal axis or a vertical axis). For example, in a treadmill where the movable member 40 is a belt, the belt may be supported a different inclinations during a workout session. Adaptive motion machines may result in movable members 40 moving through the same paths, but with different inclinations. In response to the selection of the path inclination parameter 98, controller 26 may adjust the operational characteristics of user interface 24 based upon the ongoing or current path inclination being taken by the one or more movable members 40. For example, user-interface 24 may be provided with a first operational characteristic when a movable member 40 is moving through a first path having a first inclination and may be provided with a second different operational characteristic when movable members are moving through a second path having a second inclination different than the first inclination.

In addition to providing a person with the option of selecting one of parameters 90-98 as a basis for adjusting user-interface 24, controller 26 may be further programmed to allow the person to select combinations of parameters 90-98 for use by controller 26 in the adjustment of operational characteristics of user-interface 24. For example, a person may select a combination of more than one of personal parameters personal parameters 84, a combination of more than one of movable member parameters 86, or a combination of one or more of both personal parameters 84 and movable parameters 86. Different combinations may have different predefined thresholds at which controller 26 automatically adjusts one or more operational characteristics of user-interface 24. Controller 26 may adjust one or more operational characteristic of user interface 24 differently depending upon which combination of parameters 90-98 is being used or which has been selected for use. Controller 26 may adjust user-interface 24 in a first fashion in response to the one or more thresholds for a first combination being satisfied and may adjust user-interface 24 and a second different fashion in response to one or more thresholds for a second combination being satisfied.

By way of example, during one exercise session, a person may choose both heart rate 90 and positioning 91, wherein controller 96 will adjust operational characteristics of user-interface 24 in a first fashion based upon both the heart rate of the person exercising and the sensed positioning of the person exercising during an exercise. During another exercise session, a person may choose both velocity 94 and path size 97, wherein controller 96 will adjust operational characteristics of user-interface 24 and a second fashion different than the first fashion based upon both the velocity of movable members 94 and the size of the path in which move members 94 moving. For example, controller 26 may simplify the complexity of user-interface 24 or to disable or otherwise discourage use of particular manual inputs 54 in response to the velocity 94 exceeding one or more predetermined thresholds.

By allowing multiple parameters or factors should be utilized in combination with one another as a basis for determining whether the operational characteristic of user interface 24 should be adjusted, controller 26 allows a person to fine tune when user-interface 24 is to be adjusted. For example, in instances where only velocity 94 is chosen as a parameter, controller 26 may automatically adjusts one or more operational characteristics of user-interface 24 in response to the velocity of movable member or members 40 exceeding a predefined threshold. However, if both velocity 94 and one or more of path shape 96, path size 97, or path inclination 98 are chosen, controller 26 may additionally take into account the complexity or difficulty of the path when determining whether to adjust the one or more operational characteristics of user-interface 24. If a simpler or less difficult path for one or more movable members 40 is being utilized, a higher velocity may not itself trigger automatic simplification of user-interface 24 or automatic disablement of certain manual inputs 54 of user-interface 24. In other implementations, the one or more parameters 90-98 (or other parameters) utilized by controller 26 to determine when to adjust operational characteristic of user-interface 24 may be pre-established, predefined or fixed and not selectable by a person.

Parameters 90-98 may be obtained by controller 26 either by sensing values for such parameters while the person is exercising or by consulting the exercise program currently being carried out to retrieve, determine or identify the current value for the one or more parameters. Some of parameters 90-98 may be sensed, such as a person's heart rate 90, or the person's position 91, while others, such as elapsed time 92 or workout/routine status 93, are determined using a system clock and other temporary data stored regarding the ongoing exercise session and the ongoing work out or routine being carried out. With some fitness equipment units 22, particular parameters may be continuously varied and not preset according to an ongoing exercise program. For example, with adaptive motion machines, the path shape, size and inclination may be in a continuous state of flux and not established per a predefined exercise program. In such instances, such parameters may be sensed.

With some fitness equipment units, such as treadmills, an exercise program may be controlling the velocity of the movable member 40 (the belt). In such instances, controller 26 may consult the particular exercise program being carried out to determine the velocity of the movable member 40. Sensors may not be utilized. For example, a particular exercise program for treadmill may prescribe that the velocity of the belt increase from 2 miles per hour to 5 miles per hour 3 minutes after start of the exercise session on the treadmill. By consulting the exercise program, controller 26 may determine the exact time at which the velocity is scheduled to be increased, triggering automatic adjustment of the operational characteristics of user-interface 24 in the midst of the exercise session. In other words, 3 min. after the start of the exercise session, controller 26 will adjust one or more operational characteristics of user-interface 24.

Figure 5:
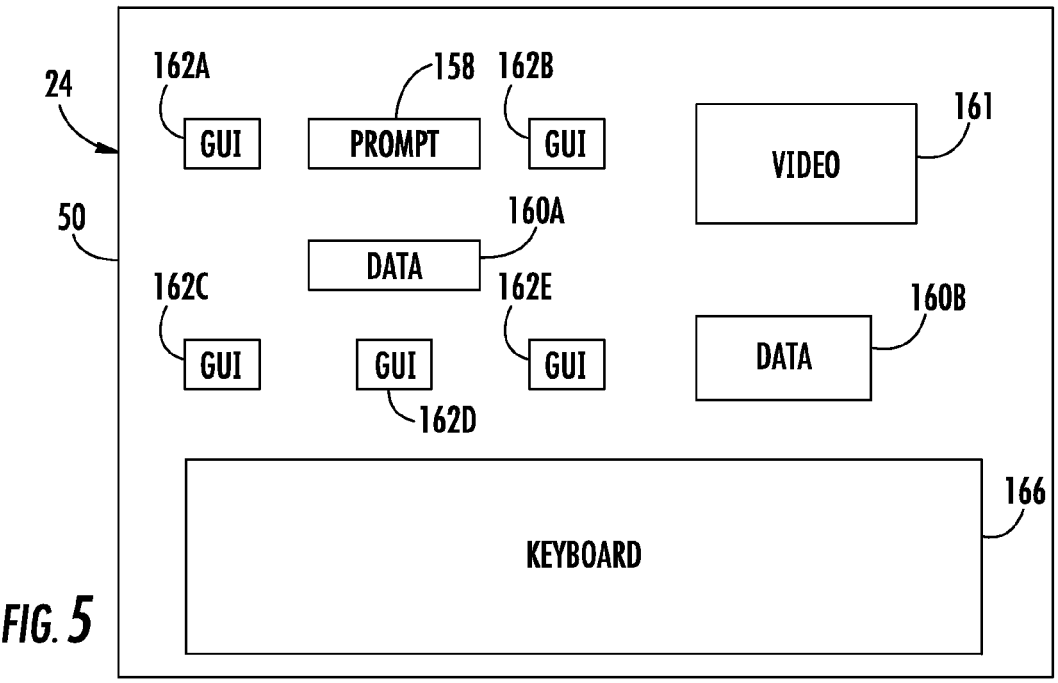
FIGS. 5 and 6 are schematic illustrations of examples of adjustments to operational characteristics of user interface 24.
Figure 6:
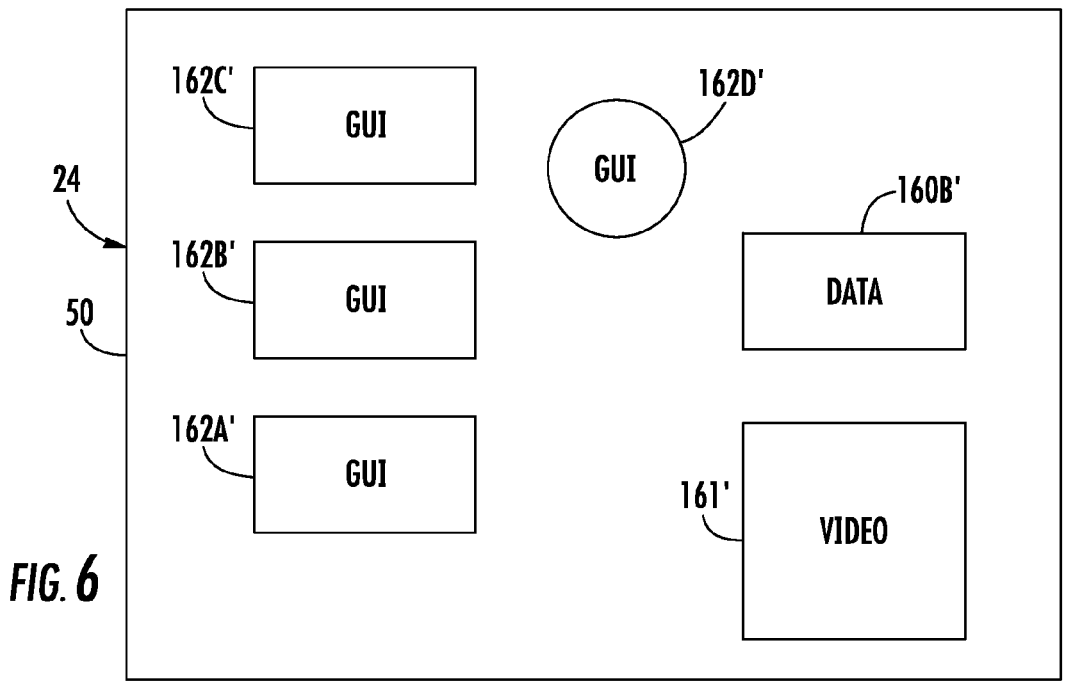

FIGS. 5 and 6 schematically illustrate one example of an adjustment of operational characteristics of user-interface 24 based upon one or more selected ongoing exercise parameters 90-98. For purposes of this disclosure, the terms "operational characteristic" or "operational characteristics" shall mean a characteristic of user-interface 24 pertaining to how interaction is provided, removed, deactivated, reduced or disabled and how or the manner in which information/data, selections (graphical user interfaces) and content is displayed or presented independent of the actual information/data, selections or content that is being presented, independent of what is actually being communicated by the content. For example, a change in the content of data or a change in content of the video is not a change in an "operational characteristic" of user-interface. An example of change in an operational characteristic of user-interface 24 is a change in how content (data, selections, video) is presented independent of the content itself. Examples of such changes to operational content comprise changes to the size, shape, rate of presentation or location of the selections (GUIs), data or content. Examples of such changes to operational characteristics of a user-interface 24 further comprise removal, deactivation or disablement of one or more selections (GUIs) as well as removal, deactivation or disablement of a manual input device (such as a keyboard (virtual or physical), keypad, mouse, stylus and the like) used to interact with a display screen or GUIs on the display screen.

FIG. 5 schematically illustrates a display screen 50 prior to adjustment of its operational characteristics by controller 26. FIG. 6 schematically illustrates display screen 50 after its adjustment of one or more operational characteristics by controller 26 based upon one or more ongoing exercise parameters. As shown by FIG. 5, display screen 50 presents prompt 158, data regions 160A and 160B, video region 161, and graphical user interfaces 162A, 162B, 162C, 162D and 166. Although each of prompt 158, data regions 160A, 160B, graphical user interfaces 162A-162D and 166, and video region 177 are schematically illustrated, the relative size, shape and location of such displayed elements is represented by the relative size, shape and location of the boxes schematically illustrating such displayed elements. Prompt 158, data regions 160A, 160B, video region 161, and graphical user interfaces 162A-162D and 166 correspond to prompt 58, data region 60, video region 161, graphical user interface 62, and graphical user interface 66 (the keyboard), respectively, and are described above.

As shown by FIG. 6, in response to one or more exercise parameters having values satisfying one of more predefined thresholds, controller 26 adjust the operational characteristics of user-interface 24 and in particular display screen 50. As shown by FIG. 6, the virtual keyboard provided by graphical user interface 166 has been disabled. In the example illustrated, the graphical user interface 166 providing a keyboard in FIG. 5 is no longer shown or presented by display screen 50. By no longer presenting keyboard 166, the disablement of keyboard 166 is visually indicated to deter a person from even attempting to utilize such a keyboard 166.

In other implementations, the keyboard provided by graphical user interface 166 may remain, but may still be disabled or deactivated by controller 52 or controller 26, no longer accepting input based upon interactions with keyboard 166. In some implementations, the presentation of the graphical user-interface depicting the keyboard may remain, but may be crossed out or otherwise visibly indicated as being disabled. By disabling or eliminating the graphical user interface 166 representing a keyboard, the person exercising may be less tempted to engage in distracting and complex interactions with such a keyboard during difficult or strenuous exercise upon fitness equipment unit 22, encouraging the person exercising to maintain his or her attention or focus on his or her interaction with the one or more movable members 40 rather than the depicted keyboard.

In some implementations in which a physical keyboard 80 or other of the manual inputs 54 is utilized as part of the exercise system 20, controller 26 may disable the physical keyboard 80 or the other manual inputs 54 based upon ongoing exercise parameters. For example, in one implementation, in response to movable member 40 (such the treadmill) having a velocity and/or inclination that exceeds or otherwise satisfies a predetermined threshold or group of thresholds, controller 26 may disable the physical keyboard 80 and/or may disable other of manual inputs 54. As a result, the person exercising may be more likely to maintain his or her focus or attention on his or her interaction with movable member 40.

As further shown by FIG. 6, the overall display of screen 50 is simplified with the enlargement of graphical user interfaces 162A-162D (shown in FIG. 5) to 162A'-162D', and the enlargement of data region 160B and video region 161 (shown in FIG. 5) to data region 160B' and video region 161', respectively. In each of such instances, the nature of the content or selections being presented by such displayed elements does not change. In particular, the function initiated or carried out with the selection of graphical user interfaces 162A'-162D' is identical to the function initiator carried out with the selection of graphical user interfaces 162A-162D, respectively. The general nature of the data being displayed by data region 160B' is identical to the nature of the data displayed by data region 160B. The general nature of the video being presented by video 161' is the same as video region 161, but merely enlarged.

In one implementation, such enlargement of the data region may involve both an enlargement of the area of the display screen 50 dedicated to the data region as well as an enlargement of the data itself being presented. For example, such an enlargement may increase the area of the display screen displaying data by at least 20%, wherein the font of the content or data being presented in data region is also enlarged. In another implementation, such enlargement of the data region may maintain the area of the display screen dedicated to displaying the data are content at the same size, but wherein the size or font of the data presented in the region or window is enlarged or magnified. In such a circumstance, the data being presented in the data region may be scrolled, streamed or otherwise restructured to accommodate the larger font size of the data in the size unchanged data region or window. In some implementations, the overall area of the data region may remain the same, but it's shape may be changed to accommodate larger font size of the data. In yet another implementation, the size or area of the data region 58 may be enlarged while the font of the data presented in the data region or window remains the same.

In one implementation, a change in the operational characteristics of user-interface 24 may additionally or alternatively include a reduction in the rate at which data or selections are visibly presented. For example, in implementations where data is scrolled or periodically changed on display screen 50, controller 26 may increase or decrease the rate of scrolling or the rate at which such data or selections (GUI's) are exchanged or visibly presented on display screen 50 based upon the exercise parameters. By way of a specific example, if controller 26 determines that the person is exercising at an exertion level exceeding a predefined threshold or is moving through a path or positioned where viewing of display screen 50 may be more difficult, controller 26 may generate control signals causing the rate at which data or selections are presented on display screen 50 to be slowed or reduced.

In addition to being enlarged, such displayed regions or elements are also rearranged and/or reshaped. In the example illustrated, display screen 50 is further simplified by removing data region 160A and graphical user interface 162E. Graphical user interface 162C' is moved to a location above graphical user interface 162A. Video region 161' is relocated below data region 160B'. Lastly, in addition to being enlarged and relocated in the overall arrangement of displayed elements, the shape of graphical user interface 162D is changed (schematically represented by the changing from a rectangle to a circle).

Controller 26 carries out such operational characteristic adjustments of user-interface 24 to enhance interaction with such displayed elements. For example, those graphical user interfaces that are more frequently interacted with or that correspond to more critical or important selections or functions are enlarged, enhancing the ability of a person to view such graphical user interfaces and enhancing the ability of a person to touch (as with a touchscreen) or to locate a cursor or pointer over the graphical user interface (using a manual input 54). To further enhance interactions, such graphical user interfaces that are determined to be more frequent interacted with or that correspond to more critical or important selections may be rearranged to locations of greater prominence on screen 50 and/or may be reshaped for easier selection or more visually prominent shapes.

Similar to the adjustment of graphical user interfaces 162, the sizing and location of data region 160 and video region 161 may be adjusted to emphasize (or deemphasize) such displayed elements. For example, video region 161 may be enlarged or shrunk depending upon the value of the content being displayed by the video. Likewise, data region 160B may be enlarged or shrunk depending upon the value of the content being presented by the data region. The relative locations of data region 116 and video region 162 may be chosen depending upon the deemed value of the content being presented by such regions or the determined tendency of such content to detrimentally distract the person while exercising.

Figure 7:
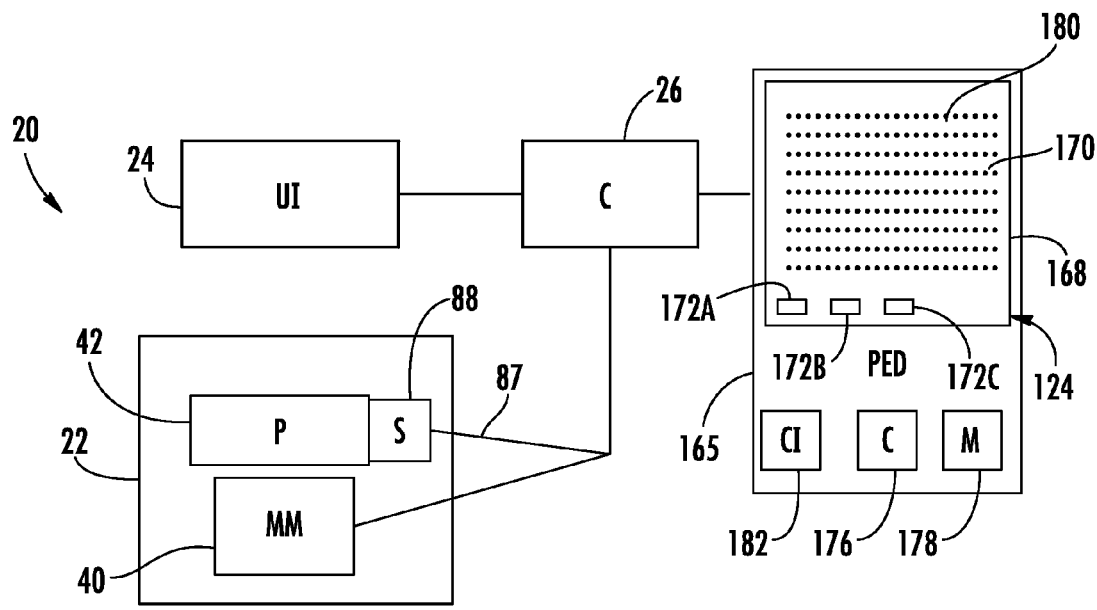
FIG. 7 is a schematic illustration of another example implementation of the exercise system of FIG. 1 additionally including a portable electronic device.

FIG. 7 schematically illustrates exercise system 20 (described above with respect to FIG. 1 additionally including portable electronic device 165 (also schematically illustrated). Portable electronic device 165 is configured to be portable in nature so as to be capable of being manually carried from one location to another. Examples of portable electronic device 165 include, not limited to, a personal data assistant (PDA), laptop, notebook computer, tablet computer (e.g. IPAD), e-reader (e.g., KINDLE), MP3 player (e.g., IPOD TOUCH).

In the example illustrated, portable electronic device 165 comprises a data region 170 and graphical user interfaces 172. In the example illustrated, graphical user interfaces 172 are presented on a display screen 168, at least portions of which serve as a touchscreen. The operation of data region 170 and graphical user interfaces 172 under the control of a controller 176 following instructions contained in a memory 178. In one implementation, the data 180 being displayed on data region 170 is stored in memory 178. In another implementation, the data 180 being presented in data region 170 is received through a communication interface 182 which, in one implementation, may comprise a flash card slot, port or antenna for receiving data 180 in a wired or wireless fashion from an external source, such as the Internet, a host computer or other external sources. The content of data 180 is independent or unrelated to the ongoing exercise, what is merely informational or provided for entertainment purposes. For example, in one implementation, data 180 may comprise an electronic version of a magazine article, a newspaper, a book and the like.

As schematically shown by FIG. 7, controller 26 is in communication with portable electronic device 165 through communication interface 182 or through another communication interface. In addition to controlling and adjusting operational characteristics of user interface 24 (described above), controller 26 additionally generate control signals which are transmitted to portable electronic device 165 and which adjusts operational characteristics of user-interface 124 of portable electronic device 165 based upon exercise parameters (described above).

Figure 7A:
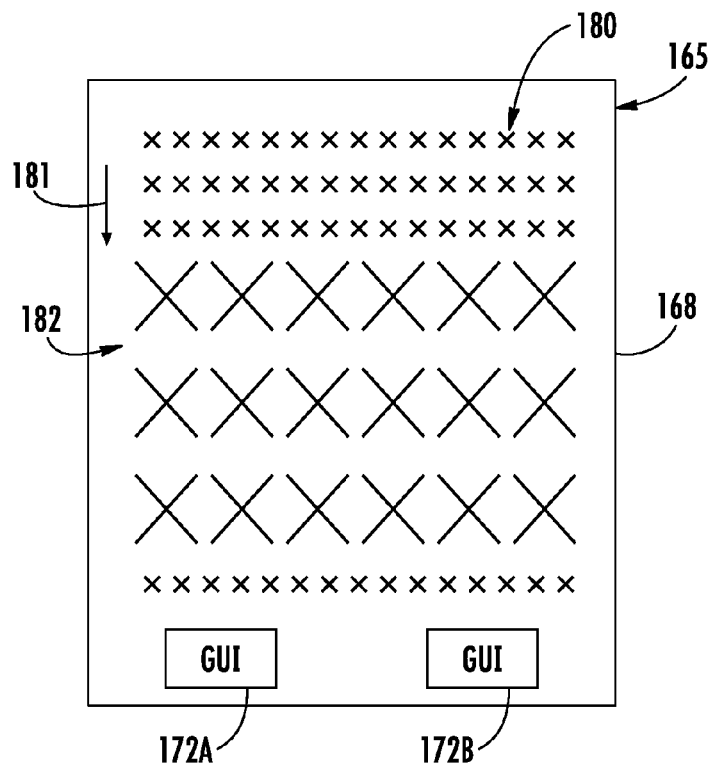
FIG. 7A is a schematic diagram of a changed user interface display screen of the portable electronic device of FIG. 7.

FIG. 7A schematically illustrates one example set of adjustments to the operational characteristics of user-interface 124 carried out by controller 26 in response to one or more exercise parameters. In the example illustrated, the alphanumeric characters, text or words are schematically represented by x's the size of such x's representing the size or font of the characters. As shown by FIG. 7A, in response to one or more exercise parameters, controller 26 generates control signals which cause or direct controller 176 of portable electronic device 165 to adjust the operational characteristics of user-interface 124. In the example illustrated, at least portions of data 180 and data region 170 of display screen 168 are enlarged to facilitate reading. In the example illustrated, the presentation of data 180 is also changed or adjusted. In the example illustrated, instead of being presented in pages, controller 26 adjusts the presentation such that data 180 across display region 170 in the direction indicated by arrow 181. Data 180 contained in the central portions 182 are enlarged (the font size is increased). In other implementations, data may be continued to be presented in a page by page format wherein the user controls the flipping of the virtual pages.

As further shown by FIG. 7A, the number of graphical user interfaces 172 is reduced while the size of the remaining graphical user interfaces 172A and 172B is enlarged to facilitate easier interaction. For example, in one implementation, such graphical user interface may be used to flip between such virtual pages or to control the rate at which data 180 is scrolled or otherwise presented. The enlargement of such graphical user interface 172 facilitates easier interaction to make such adjustments. In other implementations, controller 26 because are direct changes to the operational characteristics of user-interface 124 based upon exercise parameters in other manners.

In one implementation, a change in the operational characteristics of user-interface 124 may additionally or alternatively include a reduction in the rate at which the reading content or text of data 180 is visibly presented. For example, in implementations where data is scrolled or periodically changed on display screen 168, controller 26 may increase or decrease the rate of scrolling or the rate at which such data or selections (GUI's) are exchanged or visibly presented on display screen 168 based upon the exercise parameters. By way of a specific example, if controller 26 determines that the person is exercising at an exertion level exceeding a predefined threshold or is moving through a path or positioned where viewing of display screen 168 may be more difficult, controller 26 may generate control signals causing the rate at which data 180 is presented on display screen 168 to be slowed or reduced.

FIGS. 8-11 illustrate exercise system 220, a particular example of exercise system 20. As shown by FIG. 7, exercise system 220 comprises fitness equipment unit 222, user interface 224 and controller 26 (schematically illustrated in FIG. 7). In the example illustrated, fitness equipment unit 222 comprises a treadmill having a movable member 240 comprising a driven belt upon which a person walks, jogs or runs in place. Fitness equipment unit 222 further includes a sensor 223 configured to sense movement and positioning of movable member 240, wherein such movement and positioning provide velocity and inclination values to controller 26 for use by controller 26 and determining when to automatically adjust operational characteristics of user interface 224. In other implementations, controller 26 may obtain such velocity and inclination values directly from an exercise program being carried out during exercise.

In the example illustrated, user interface 224 comprises a control and display panel provided as part of the fitness equipment unit 222. Controller 26 is described above with respect to exercise system 20. In one implementation, controller 26 and user-interface 224 are embodied as a single unit, wherein controller 26 controls user-interface 224 as well as one or more functions of fitness equipment unit 222. In another implementation, controller 26 may be provided remotely from user-interface 224 and fitness equipment unit 222, wherein controller 26 communicates with user-interface 224 and fitness equivalent unit 222 across a wired or wireless connection. In one implementation, controller 26 may be provided at the fitness equipment facility housing fitness community 222. In another implementation, controller 26 may be located in what is known as the "cloud".

Figure 9:
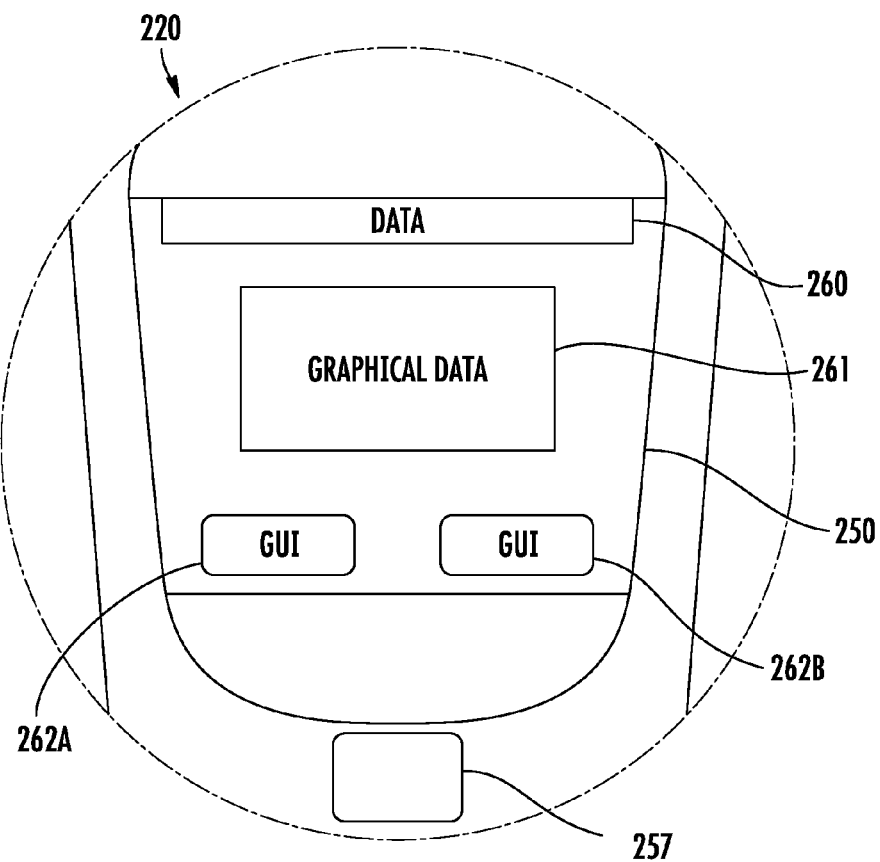
FIG. 9 is an enlarged fragmentary view of a user interface of the system of FIG. 7.
Figure 8:
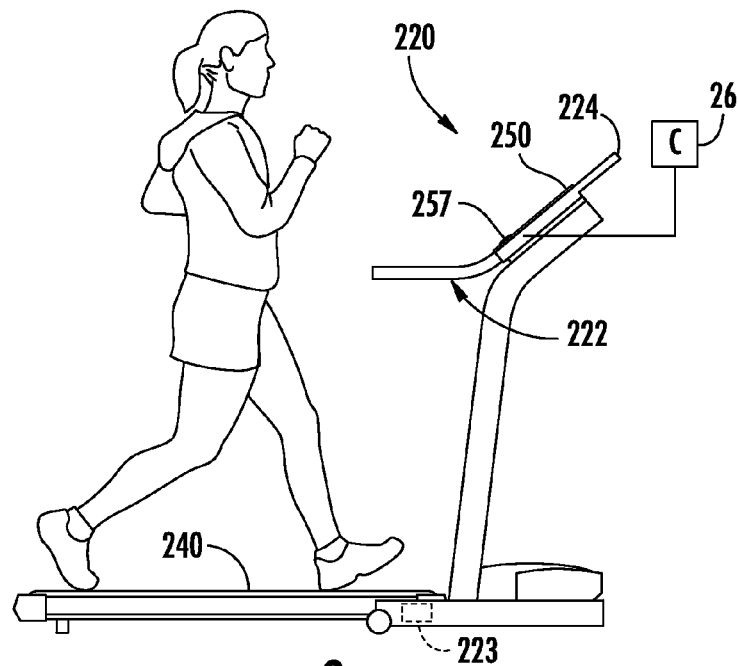
FIG. 8 is a front perspective view of an example implementation of the exercise system of FIG. 1.

FIG. 9 is an enlarged view of user-interface 224 at one example point time during an ongoing exercise by a person (not shown) on movable member 240. As shown by FIG. 8, user interface 224 comprises a manual pushbutton 257 and a touchscreen 250 which includes a data region 260, a graphical data display 261 and a graphical user interfaces 262A and 262B. In one implementation, manual pushbutton 257 activates and deactivates user input 224. Data region 260 provides information or data in the form of alpha-numeric symbols for text. In the example illustrated, data region 265 present such data in the form of a stream of data continuously moving across display screen 250. Graphical display 261 provides a graphic display of results or an exercise program being executed. For example, in one implementation, graphical display 261 comprises a series of LED bars illustrating changes in inclination of movable member 240. Graphical user interfaces 262A and 262B comprise graphical icons which upon being manually touched or contacted provide signals that serve as input to controller 26 to adjust the operation of fitness equipment unit 222 or the information being presented on screen 250. In other implementations, user-interface 224 may include other displayed elements having other sizes, locations and functions.

Figure 11:
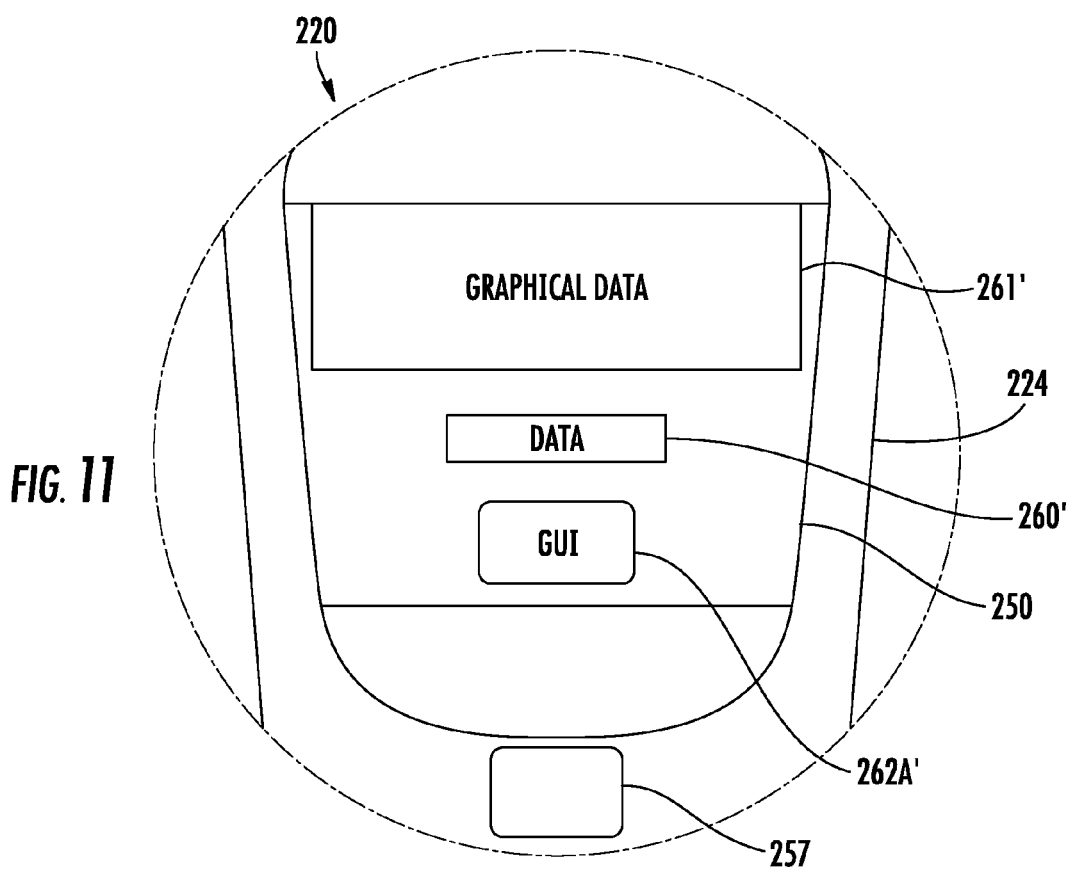
FIG. 11 is an enlarged fragmentary view of the user interface of the system of FIG. 8 illustrating a change to the operational characteristics of the user interface based upon the change in the inclination and velocity of the movable member.
Figure 10:
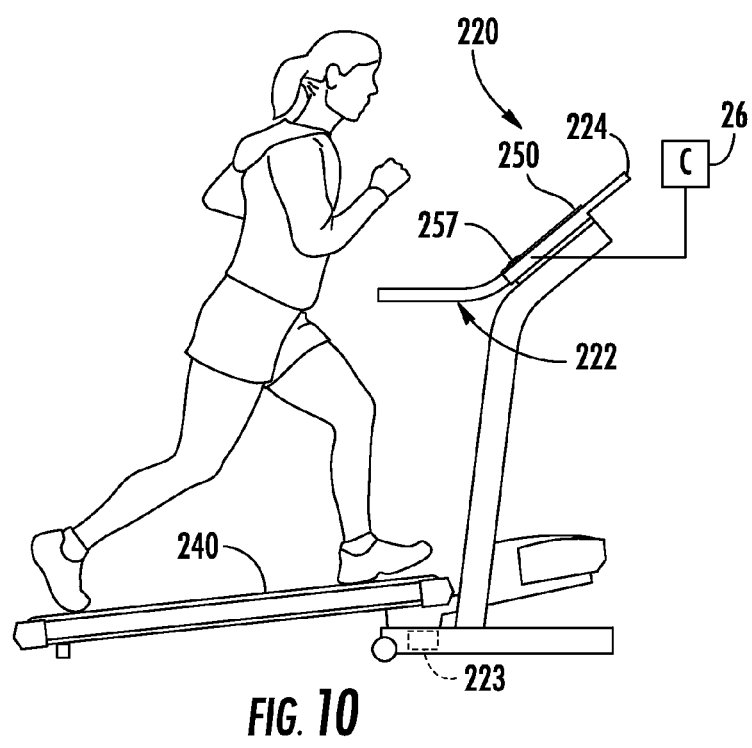
FIG. 10 the front perspective view of the exercise system of FIG. 7 illustrating a change in inclination and velocity of a movable member.

FIGS. 10 and 11 illustrate exercise system 220 with working member 240 moved to a different inclination (the new greater inclined position 240' being shown in broken lines) and with movable member 240 being driven at a greater velocity. In the example shown in FIGS. 9 and 10, controller 26 programmed or configured to adjust operational characteristics of user interface 224 based upon one or both of the ongoing current velocity and inclination of movable member 240. As shown by FIG. 10, in response to inclination and velocity of movable member 240 exceeding predefined thresholds, controller 26 adjust the operational characteristics of user interface 224. In the example shown in FIG. 10, data region 260 is relocated, resized and reconfigured as data region 260'. Instead of the data being presented as a stream of data, data is presented in a more stationary manner at data region 260' towards a central area of display screen 250. Graphical display 261 is slightly enlarged and move to an upper portion of display screen 250 for enhanced viewing. Graphical user interface 262B is no longer presented while graphical user interface 262A is enlarged and centered to simplify manual interaction with the graphical user interface. As a result, interaction with user-interface 224 is enhanced or maintained despite the potentially more difficult environment in which movable member 240 has a greater inclination and is moving at a greater speed.

As further shown by FIGS. 8 and 10, in response to the increased inclination of working member 240, a person exercising naturally leans forward towards user interface 224. At the same time, in some implementations, user-interface 224 is pivoted in a counter-clockwise direction towards the person exercising. As a result, the persons orientation and positioning with respect user interface 224 changes. Controller 26 adjust one or more operational characteristics of user interface 224 taking into account the new relative positioning of user-interface 224 and the person's positioning. In some implementations, controller 26 may adjust operational characteristics of user interface 224 multiple times depending upon a degree of inclination of movable member 240. For example, in one implementation, the size of a graphical user interfaces 262 may be increased to facilitate easier interaction will the size or font of the data being presented may be slightly decreased to allow the visible display of a greater amount of information. In other implementations, operational characteristics of user-interface 224 may be adjusted in other manners by controller 26 depending upon the sensed or identified inclination of movable member 240.

FIGS. 12-15 illustrate exercise system 320, an example implementation of exercise system 20. As shown by FIG. 12, exercise system 320 comprises fitness equipment unit 322, user interface 324 and controller 26 (schematically illustrated). In the example illustrated, fitness equipment unit 322 comprises a stationary bicycle having a movable members 340 comprising a foot pedals for being driven by the person's feet. Fitness equipment unit 322 further includes a sensor 323 configured to sense movement and positioning of movable members 340, wherein such movement and positioning provide velocity values to controller 26 for use by controller 26 and determining when to automatically adjust operational characteristics of user interface 324. In other implementations, controller 26 may obtain such velocity values directly from an exercise program being carried out during exercise.

As further shown by FIG. 12, fitness equipment unit 322 additionally includes sensors 327, 329. Sensors 327, 329 output signals to controller 26 in response to contact or engagement by a person's anatomy (hands). One implementation, sensors 327, 329 may additionally detect a person's pulse or heart rate. Sensors 327, 329 are utilized by controller 26 to identify or determine the positioning, posture or orientation of the person 342 on fitness equipment unit 322. In the example illustrated, when engaged by person 342, sensor 327 indicates to controller 26 that the person 342 is in an upright position or posture. When engaged by person 342, sensor 329 indicates to controller 26 that the person 342 is in a declined or leaning orientation, position or posture. Alternatively, the absence of the signal from sensor 329 may indicate that person 342 is an upright posture. In yet another implementation, it is of signals from both sensors 327, 329 may indicate that leaning forward posture. In other implementations, sensors 327, 329 may alternatively be configured to emit signals until contacted are engaged by a person's anatomy.

In the example illustrated, user interface 224 comprises a control and display panel provided as part of the fitness equipment unit 222. Controller 26 is described above with respect to exercise system 20. In one implementation, controller 26 and user-interface 324 are embodied as a single unit, wherein controller 26 controls user-interface 324 as well as one or more functions of fitness equipment unit 322. In another implementation, controller 26 may be provided remotely from user-interface 324 and fitness a community 322, wherein controller 26 communicates with user-interface 324 and fitness equivalent unit 322 across a wired or wireless connection. In one implementation, controller 26 may be provided at the fitness equipment facility housing fitness equipment unit 322. In another implementation, controller 26 may be located in what is known as the "cloud".

FIGS. 13 and 15 illustrate the automatic adjustment of operational characteristics of user interface 324 by controller 26 based upon the sensed positioning of person 342. As shown by FIG. 13, when sensors 327, 329 indicate to controller 26 that person 342 is an upright orientation during exercise, controller 26 may adjust the operational characteristics of user interface 324 such that data region 360 is presented vertically higher (above a vertical midpoint in the example illustrated), near an upper portion of display screen 50. Alternatively, when sensors 327, 329 indicate to controller 26 that person 342 is in a leaning forward orientation during exercise, controller 26 may adjust the operational characteristics of user interface 324 such that data region 360' is presented vertically lower, near an lower portion (below a vertical midpoint in the example illustrated) of display screen 50. Although not illustrated, controller 26 may also be configured to automatically adjust other operational characteristics of user interface 324 based upon the positioning of person 342 as well as based upon other parameters, such as the velocity of movable members 340 as sensed by sensor 323 or obtained from the particular exercise program being carried out.

FIGS. 16-18 illustrate exercise system 420, another example implementation of exercise system 20. As shown by FIG. 16, exercise system 420 comprises fitness equipment unit 422, user interface 424 and controller 26 (schematically illustrated). In the example illustrated, fitness equipment unit 422 comprises an adaptive motion machine or adaptive motion trainer having movable members 440 comprising a foot pedals for being driven by the person's feet. Fitness equipment unit 422 further includes one or more sensors 423 configured to sense movement and positioning of movable members 440, wherein such movement and positioning provide velocity values to controller 26 determining velocity and path parameters (shape, size, inclination) for use by controller 26 in determining when to automatically adjust operational characteristics of user interface 324. In other implementations, controller 26 may obtain such velocity values directly from an exercise program being carried out during exercise. As shown by FIG. 16, fitness equipment unit 422 is configured to allow a person to instantaneously change the path of movable members 440 by simply applying different force to movable members 440. In the example illustrated, two example paths 443A, 443B are illustrated.

FIGS. 17 and 18 illustrate the automatic adjustment of operational characteristics of user interface 424 by controller 26 based upon the sensed path being taken by movable members 440. As shown by FIG. 16, when sensors 423 indicate to controller 26 that movable members 440 are taking path 443A (a more inclined path), controller 26 may adjust the operational characteristics of user interface 324 such that data region 460 is presented vertically higher (above a vertical midpoint in the example illustrated), near an upper portion of display screen 50. Alternatively, when sensors for 23 indicate to controller 26 that movable members 440 are taking path 443B (a more declined path), controller 26 may adjust the operational characteristics of user interface 424 such that data region 460' is presented vertically lower, near an lower portion (below a vertical midpoint in the example illustrated) of display screen 50. Although not illustrated, controller 26 may also be configured to automatically adjust other operational characteristics of user interface 424 based upon characteristics of the adjustable path being taken by movable members 440 as well as based upon other parameters, such as the velocity of movable members 440 as sensed by sensors 423 or obtained from the particular exercise program being carried out.

FIG. 19 illustrates exercise system 520, another example implementation of exercise system 20 described above. As shown by FIG. 19, exercise system 520 comprises fitness equipment unit 522, user interface 524 and controller 26 (schematically illustrated). In the example illustrated, fitness equipment unit 522 comprises an elliptical machine or device having a movable members 540 comprising a foot pedals for being driven by the person's feet. In addition to movable members 540, fitness equipment unit 522 comprises a base or frame 600, flywheel or crank arm 602, foot links 604R, 604L (collectively referred to as foot links 604), forward tracks or ramps 606 (collectively referred to as ramps 606, ramp 606L (the left side ramp) not shown), and lift mechanism 608. Although not illustrated, in some implementations, the elliptical machine serving as fitness equipment unit 520 may additionally include swing arms.

Frame 600 serves as a foundation for the rest of unit 522. Crank arm 602 comprises a disk or wheel rotatably supported by frame 600 for rotation about axis 610. Foot links 604 are pivotably connected to crank arm 602 at eccentric locations so as to rotate 180 degrees out of phase with respect to one another about axis 610. Foot links 604 are connected to crank arm 602 at a first end and slide or roll up and down ramps 606 at a second end while supporting movable members 540 between the first end and the second end. Ramps 606 provide paths or tracks along which the forward end of foot links 604 slide or roll. In the example illustrated, ramp 606 are each pivotally supported by frame 600 for pivotal movement about axis 612 between one of multiple selectable inclines or slopes.

Lift mechanism 608 comprises an actuator coupled to frame 600 and connected or in engagement with ramp 606 (or a single ramp 606 reserves both foot links 604) that is configured to pivot ramp 606 about axis 612 between the various inclinations. In the example illustrated, lift mechanism 608 comprises an electric motor driving a worm gear or screw gear to linearly raise and lower a forward portion of ramps 606. In other implementations, other actuators, such as electric solenoids or hydraulic/pneumatic cylinder-piston assemblies may be utilized to raise and lower ramps 606.

In the example illustrated, fitness equipment unit 522 further includes one or more sensors 523 configured to sense movement and positioning of movable members 540, wherein such movement and positioning provide velocity values to controller 26 determining velocity and path parameters (shape, size, inclination) for use by controller 26 in determining when to automatically adjust operational characteristics of user interface 524.

In one implementation, sensor 523 may comprise a rotary potentiometer associate with lift mechanism 608 for sensing the rotation of the screw gear to determine an inclination of ramps 606. In one implementation, sensor 523 may further be connected to crank arm 6022 sensor determine the rotation of crank arm 602 and the velocity of movement of movable members 540. In other implementations, other forms of sensors may be employed.

As shown by FIG. 19, fitness equipment unit 522 is configured to allow a person to change the path of movable members 540 by adjusting the inclination of ramps 606. In the example illustrated, three example inclinations 640A, 640B and 640C are illustrated which provide three example paths 643A, 643B, 643C, respectively. As shown on the right side of FIG. 19, during movement of movable members 540 along path 643A, a person's body and head vertically move through a distance D1. During movement of movable members 540 along path 643C, a person's body and head vertically move through a greater distance D2. This greater head bob or vertical head movement and may make it more difficult for the person to focus on data or interact with controls provided on user interface 524.

FIGS. 19A and 19B illustrate one example of the automatic adjustment of operational characteristics of user interface 524 by controller 26 based upon the sensed path (or velocity and/or inclination) being taken by movable members 540. As shown by FIG. 19A, when sensors 523 indicate to controller 26 that movable members 540 are taking path 643A (a more horizontally flat path), user-interface 524 provides data regions 660, video region 661 and the graphical user interfaces 662 (for tactile interaction such as where display screen 650 comprises a touch screen or for interaction using one or more manual inputs for manipulating a pointer to select or point to such graphical user interfaces).

As shown by FIG. 19B, in response to sensors 523 indicating that the inclination of path 643 has been increased (thereby increasing head bob) and/or the velocity has been increased, controller 26 adjust operational characteristics of user-interface 524 to 524'. In the example illustrated, a single larger data region 660 is alternatively presented, to larger and relocated graph the user interfaces 662 or alternatively presented and video region 661 is removed from display screen 650. The shape of graphical user interface 662A is further changed. As a result, controller 26 makes adjustments to operational characteristics of user-interface 524 to enhance viewing and interaction to address the increase head bob. In other implementations, controller 26 may also be configured to automatically adjust other operational characteristics of user interface 524 based upon characteristics of the adjustable path being taken by movable members 540 obtained from the particular exercise program being carried out.

Figure 20:
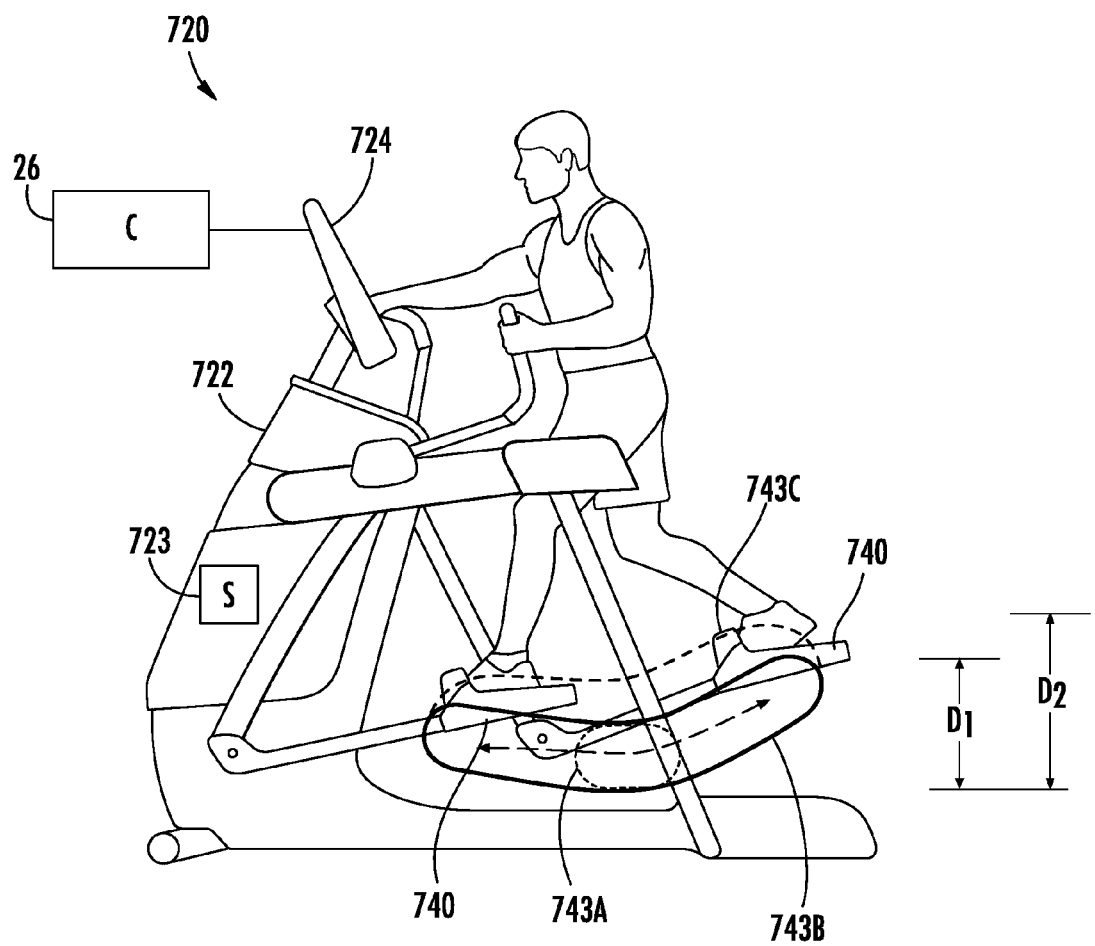
FIG. 20 is a side elevation view of another example implementation of the exercise system of FIG. 1.

FIG. 20 illustrates exercise system 720, another example implementation of exercise system 20 described above. As shown by FIG. 20, exercise system 720 comprises fitness equipment unit 722, user interface 724 and controller 26 (schematically illustrated). In the example illustrated, fitness equipment unit 722 comprises an adaptive motion machine or adaptive motion trainer (an example of which is shown and described in US Patent Publication 20100267524 by Stewart et al. which published on Oct. 21, 2010 at which is entitled EXERCISE APPARATUS WITH FLEXIBLE ELEMENT, the full disclosure of which is hereby incorporated by reference) having a movable members 740 comprising a foot pedals for being driven by the person's feet. Fitness equipment unit 422 further includes one or more sensors 723 configured to sense movement and positioning of movable members 440, wherein such movement and positioning provide velocity values to controller 26 determining velocity and path parameters (shape, size, inclination) for use by controller 26 in determining when to automatically adjust operational characteristics of user interface 724. In other implementations, controller 26 may obtain such velocity values directly from an exercise program being carried out during exercise. As shown by FIG. 20, fitness equipment unit 422 is configured to allow a person to instantaneously change the path (horizontal extent and shape) of movable members 440 by simply applying different force to movable members 440. In the example illustrated, this clearly unit 722 further provides the person exercising with the option of adjusting the vertical height or vertical extent of the path.

In the example illustrated, three example paths 743A, 743B and 743C are illustrated. As shown on the right side of FIG. 20, during movement of movable members 740 along path 643A or 643B, a person's body and head vertically move through a distance D1. During movement of movable members 540 along path 743C, a person's body and head vertically move through a greater distance D2. This greater head bob or vertical head movement and may make it more difficult for the person to focus on data or interact with controls provided on user interface 724.

FIGS. 19A and 19B (above) illustrate one example of the automatic adjustment of operational characteristics of user interface 724 by controller 26 based upon the sensed path (or velocity and/or inclination) being taken by movable members 740. As shown by FIG. 19A, when sensors 723 indicate to controller 26 that movable members 740 are taking path 743A 7, user-interface 524 provides data regions 660, video region 661 and the graphical user interfaces 662 (for tactile interaction such as where display screen 650 comprises a touchscreen or for interaction using one or more manual inputs for manipulating a pointer to select or point to such graphical user interfaces).

As shown by FIG. 19B, in response to sensors 723 indicating that the shape or vertical height of path 743 has been increased (thereby increasing head bob) and/or the velocity has been increased, controller 26 adjusts operational characteristics of user-interface 524 to 524'. In the example illustrated, a single larger data region 660 is alternatively presented, two larger and relocated graphical user interfaces 662 are alternatively presented and video region 661 is removed from display screen 650. The shape of graphical user interface 662A is further changed. As a result, controller 26 makes adjustments to operational characteristics of user-interface 524 to enhance viewing and interaction to address the increase head bob. In other implementations, controller 26 may also be configured to automatically adjust other operational characteristics of user interface 524 based upon characteristics of the adjustable path being taken by movable members 740 obtained from the particular exercise program being carried out.

Figure 21:
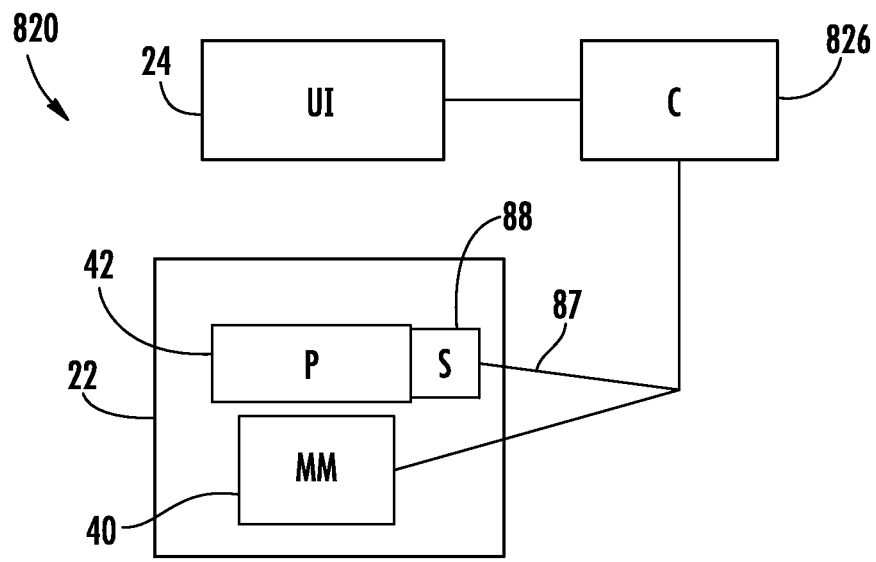
FIG. 21 is a schematic illustration of another example of an exercise system.

FIG. 21 schematically illustrates exercise system 820. Exercise system 820 is similar to exercise system 20 except that exercise system 820 include controller 826 in place of controller 26. Those components or elements of exercise system 820 which correspond to components or elements of exercise system 20 are numbered similarly. As with controller 26, controller 826 is configured to provide a first mode of operation wherein controller 26 carries out the method described in FIG. 3 (and examples of which are provided in FIGS. 2 and 4-20), wherein controller 26 dynamically adjusts one or more operational characteristics of user-interface 24 based upon obtained exercise parameters, both static and ongoing parameters. In addition, controller 826 offers another alternative user selectable mode of operation wherein controller 826 carries out method 900 illustrating FIG. 22.

Figure 22:
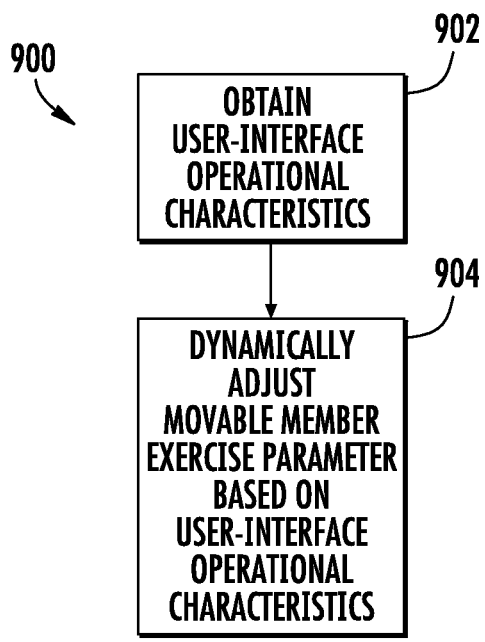
FIG. 22 is a flow diagram of a method that may be carried out by the exercise system of FIG. 21.

As indicated by step 902 in FIG. 22, controller 826 obtains one or more operational characteristics (defined above) of user interface 24. As indicated by step 904, based upon such user interface operational characteristics currently selected or in use, controller 826 dynamically adjusts one or more of movable member parameters such as one or more of the example movable member exercise parameters shown and described above with respect to FIG. 4. In one implementation, controller 826 may further determine when such adjustments to the movable member exercise parameters are made and what adjustments are made based upon additional parameters such as the example personal parameters 84 shown and described above with respect to FIG. 4. As a result, controller 826 will automatically adjust one or more parameters of movable member 40 to enhance interaction with fitness equipment unit 22 and user-interface 24. As when method 100 is being carried out by controller 826 (or controller 26), controller 826 may be programmed or configured to allow the person exercising to override such adjustments either after such adjustments are automatically made or prior to the implementation of such adjustments.

By way of example, in one implementation, a person exercising may decide to start using a keyboard (virtual or physical) to initiate an Internet search or to enter other information. In response to detecting use of the keyboard (the user-interface operational characteristic), controller 826 may automatically adjust and exercise parameter of movable member 40. For example, controller 826 may adjust the velocity at which movable member 40 is moved or is movable (parameter 94), the resistance level asserted against movement of movable member 40 (parameter 95) or a characteristic of the path in which movable member may be moved. In one implementation, controller 826 may be configured to provide a warning or notify the person exercising on user-interface 24 of the upcoming changes that will occur in response to use of particular manual input device 54 of user-interface 24. As a result, the person exercising make informed decision of whether or not to use such manual input devices 54 or may prepare himself or herself for such changes to the operation of movable member 40.

By way of a more specific example, in response to detecting use of a particular user-interface manual input device 54 (shown in FIG. 2), such as use of virtual or physical keyboard while a person is exercising on a treadmill, controller right 26 may reduce the speed at which the belt is driven and/or automatically reduce its incline. Once controller 826 determines that the person is no longer using a particular user-interface manual input device 54 (or after a predetermined delay period upon such detection), controller 826 may resume or reinstate the previous velocity and/or incline for the belt (movable member exercise parameters).

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An exercise system comprising:
   a fitness equipment unit having a movable member to be contacted by an anatomy of a person to facilitate exercise by the person;
   a user interface comprising a keyboard; and
   a controller configured to generate control signals to dynamically adjust at least one operational characteristic of the user interface, while the person is exercising, based upon at least one parameter of ongoing exercise and only after an existing operational characteristic of the user interface has been in place for a predefined non-zero period of time, wherein once the at least one operational characteristic of the user interface has been changed, further changes to the at least one operational characteristic of the user interface are prevented until the predefined non-zero period of time has expired; and
   wherein the control signals disable an input of selection to a web browser or webpage using the keyboard.

2. The exercise system of claim 1, wherein the at least one parameter of ongoing exercise further comprises a concurrent evaluation of a combination of a sensed parameter of the person exercising and a parameter of the movable member of the fitness equipment unit.

3. The exercise system of claim 2, wherein the parameter of the movable member of the fitness equipment unit is selected from a group of parameters consisting of: a velocity of the movable member; a resistance asserted against movement of the movable member; an adjustable path shape through which the movable member moves; an adjustable size of a path through which the movable member moves; and an adjustable inclination of a path through which the movable member moves.

4. The exercise system of claim 1, wherein the control signals disable use of the keyboard while the disabled keyboard remains viewable to the person exercising.

5. The exercise system of claim 1, wherein the keyboard comprises a keyboard graphical user interface and wherein the control signals remove the keyboard graphical user interface.

6. The exercise system of claim 1, wherein the user interface further comprises a graphical user interface and wherein the control signals adjust a size of the graphical user interface.

7. The exercise system of claim 1, wherein the user interface further comprises a graphical user interface and wherein the control signals adjust a location of the graphical user interface.

8. The exercise system of claim 1, wherein the user interface further comprises a display screen and wherein the at least one operational characteristic of the user interface is selected from a group of operational characteristics consisting of: a size of a graphical user interface on the display screen, a location of a graphical user interface on the display screen; a display/non-display condition of a graphical user interface on the display screen; a size of data being presented on the display screen; and a location of data being presented on the display screen.

9. The exercise system of claim 1, wherein the fitness equipment unit comprises a treadmill having a belt to contact feet of the person exercising, wherein the at least one parameter of ongoing exercise comprises at least one of a velocity and an inclination of the belt.

10. The exercise system of claim 1, wherein the fitness equipment unit offers a plurality of available positions for the person during the ongoing exercise, wherein the user interface further comprises a display screen and wherein the control signals adjust a location of data being presented on the display screen based upon a sensed determination of which of the plurality of available positions on the fitness equipment unit being taken by the person, wherein the control signals rearrange a relative location of the data being presented on the display screen such that first data being presented above second data on the display screen is rearranged to be presented below the second data on the display screen.

11. The exercise system of claim 1, wherein the fitness equipment unit comprises a stationary bicycle having handgrips configured to be grasped when a person is leaning forward, wherein at least one of the handgrips includes a sensor to sense gripping, wherein the user interface further comprises a display screen and wherein the control signals adjust a location of data being presented on the display screen to a lower portion of the display screen in response to the sensed gripping of the at least one of the handgrips.

12. The exercise system of claim 1, wherein the at least one parameter of ongoing exercise comprises a current workout intensity of ongoing exercise.

13. The exercise system of claim 1, wherein the user interface is provided as part of a portable electronic device and wherein the controller is configured to generate control signals adjusting at least one operational characteristic of the user interface of the portable electronic device.

14. The exercise system of claim 1, wherein the controller is further configured to receive signals indicating selection of the at least one parameter of ongoing exercise, by the person, from a plurality of available parameters, to be used as a basis for dynamically adjusting the at least one operational characteristic of the user interface while the person is exercising.

15. The exercise system of claim 1, wherein the at least one parameter of ongoing exercise comprises a combination of multiple parameters of ongoing exercise.

16. The exercise system in clam 1, wherein the user interface further comprises a display screen and wherein dynamic adjustment of the at least one operational characteristic is selected from a group of adjustments consisting of: changing a rate at which data is presented on the display screen and changing a format of data presentation between scrolling of data and presenting data in a page format.

17. The exercise system in claim 1, wherein the at least one parameter of ongoing exercise comprises a parameter of the movable member selected from a group of parameters consisting of: a resistance asserted against movement of the movable member; an adjustable path shape through which the movable member moves; an adjustable size of a path through which the movable member moves; and an adjustable inclination of a path through which the movable member moves.

18. The exercise system in claim 1, wherein the controller is further configured to:
- receive signals indicating selection of the at least one parameter of ongoing exercise, by the person, from a plurality of different available parameters, for use in dynamically adjusting the at least one operational characteristic of the user interface;
- obtain a value of the at least one selected parameter of ongoing exercise; and
- dynamically adjust the at least one operational characteristic of the user interface based upon the obtained value of the at least one selected parameter of ongoing exercise.

* * * * *